(12) United States Patent
Hosoda et al.

(10) Patent No.: US 8,497,252 B2
(45) Date of Patent: Jul. 30, 2013

(54) COMPOSITIONS COMPRISING CARDIAC STEM CELLS OVEREXPRESSING SPECIFIC MICRORNAS AND METHODS OF THEIR USE IN REPAIRING DAMAGED MYOCARDIUM

(75) Inventors: Toru Hosoda, Chestnut Hill, MA (US); Piero Anversa, Boston, MA (US); Annarosa Leri, Boston, MA (US); Jan Kajstura, Brookline, MA (US)

(73) Assignee: New York Medical College, Valhalla, NY (US)

( * ) Notice: Subject to any disclaimer, the term of this patent is extended or adjusted under 35 U.S.C. 154(b) by 0 days.

(21) Appl. No.: 13/487,974

(22) Filed: Jun. 4, 2012

(65) Prior Publication Data

US 2013/0017176 A1      Jan. 17, 2013

Related U.S. Application Data

(63) Continuation of application No. 12/480,861, filed on Jun. 9, 2009, now Pat. No. 8,193,161.

(60) Provisional application No. 61/059,936, filed on Jun. 9, 2008.

(51) Int. Cl.
*C12N 15/11* (2006.01)
*C12N 5/02* (2006.01)
*A61K 35/12* (2006.01)

(52) U.S. Cl.
USPC ........... 514/44 R; 424/520; 435/325; 977/913

(58) Field of Classification Search
None
See application file for complete search history.

(56) References Cited

U.S. PATENT DOCUMENTS

| | | |
|---|---|---|
| 7,862,810 B2 | 1/2011 | Anversa |
| 2003/0054973 A1 | 3/2003 | Anversa |
| 2006/0239983 A1 | 10/2006 | Anversa |
| 2006/0246491 A1 | 11/2006 | Srivastava |
| 2007/0204351 A1 | 8/2007 | Davidson et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0180998 A1 | 7/2009 | Anversa et al. |
| 2009/0186414 A1 | 7/2009 | Srivastava et al. |
| 2010/0239538 A9 | 9/2010 | Anversa et al. |

FOREIGN PATENT DOCUMENTS

| | | |
|---|---|---|
| WO | WO 03/0103611 A2 | 12/2003 |
| WO | WO 2004113380 A2 | 12/2004 |
| WO | WO 2005/000403 A2 | 1/2005 |
| WO | WO 2007/070483 A2 | 6/2007 |

OTHER PUBLICATIONS

Nguyen et al., Current Opinion in Molecular Therapeutics 2008 10(2):158-167.*
Howard et al., Expert Opin. Biol. Ther. (2007) 7(12).*
Zhang et al., Journal of Molecular and Cellular Cardiology 44 (2008) 281-292.*
Suarez et al., "Dicer dependent microRNAs regulate gene expression and functions in human endothelial cells," *Circulation Research*, Apr. 2007, 100(8): 1164-1173.
Boutz et al., "MicroRNAs regulate the expression of the alternative splicing factor nPTB during muscle development," *Genes. Dev.* Jan. 2007, 21(1):71-84.
Young, International Search Report based on International Application No. PCT/US2009/046667 (Sep. 17, 2009).
Care et al., "MicroRNA-133 controls cardiac hypertrophy," Nature Medicine, vol. 13(5):613-618, 2007.
Joggerst and Hatzopolous, "Stem cell therapy for cardiac repair: benefits and barriers," Expert Reviews in Molecular Medicine, vol. 11:1-19, 2009.
Bearzi et al., "Human cardiac stem cells," Proc. Natl. Acad. Sci. USA, vol. 104: 14068-14073, 2007.
Beltrami et al., "Adult cardiac stem cells are multipotent and support myocardial regeneration," Cell, vol. 114: 763-776, 2003.
Thum et al., "MicroRNAs: novel regulators in cardiac development and disease," Cardiovascular Research, vol. 79: 562-570, 2008.
Fey-Lamprecht, Supplementary European Search Report for European Application No. 09763402.6, 9 pages, European Patent Office, Munich, mailed Dec. 3, 2012.

\* cited by examiner

*Primary Examiner* — Doug Schultz
(74) *Attorney, Agent, or Firm* — Cooley LLP

(57) ABSTRACT

The invention provides compositions comprising modified stem cells containing a transgene that affects the expression of at least one gene that inhibits or promotes cardiomyogenesis. In particular, the invention discloses compositions comprising cardiac stem cells, wherein said cardiac stem cells comprise a transgene encoding a microRNA. The compositions of the invention find use in the treatment of cardiovascular disorders, such as myocardial infarction. Methods of repairing damaged myocardium in a subject using the modified stem cells are also disclosed.

19 Claims, 12 Drawing Sheets

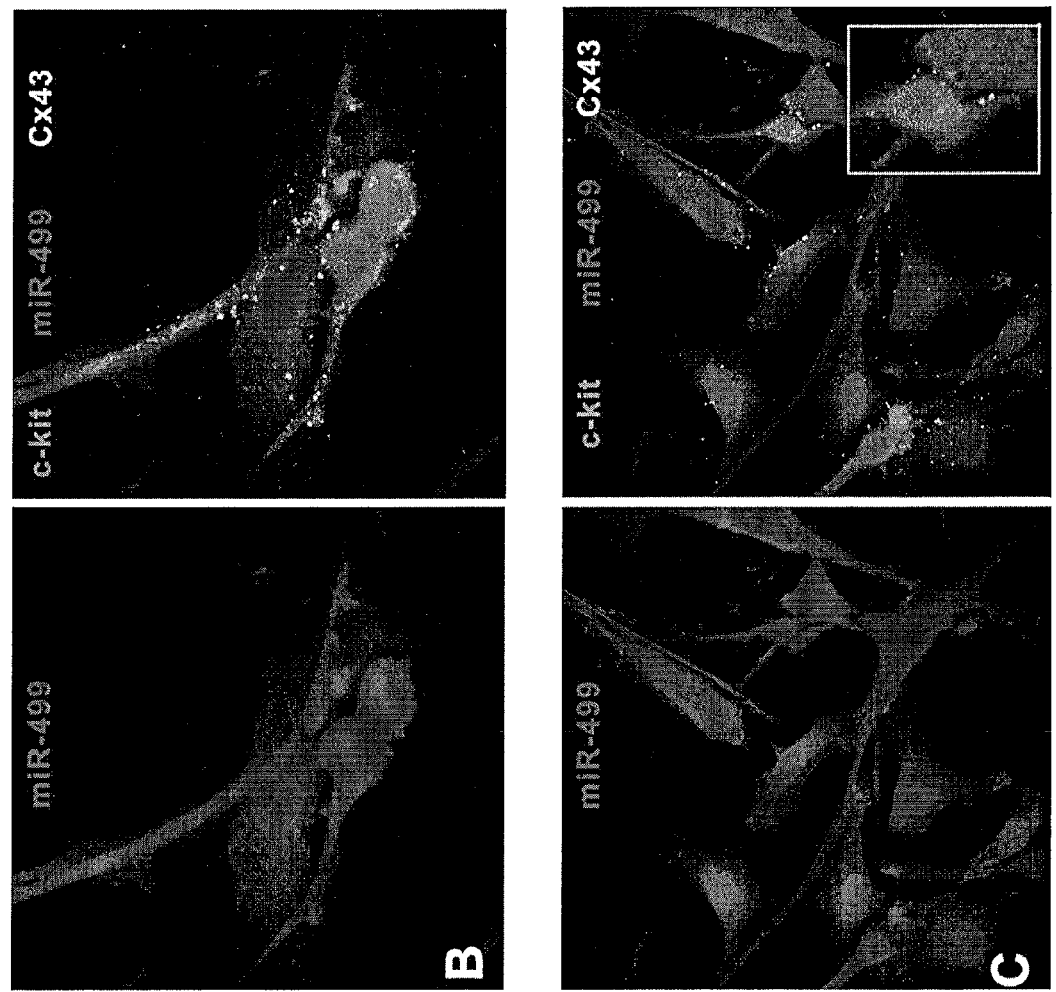
Figure 6 B, C

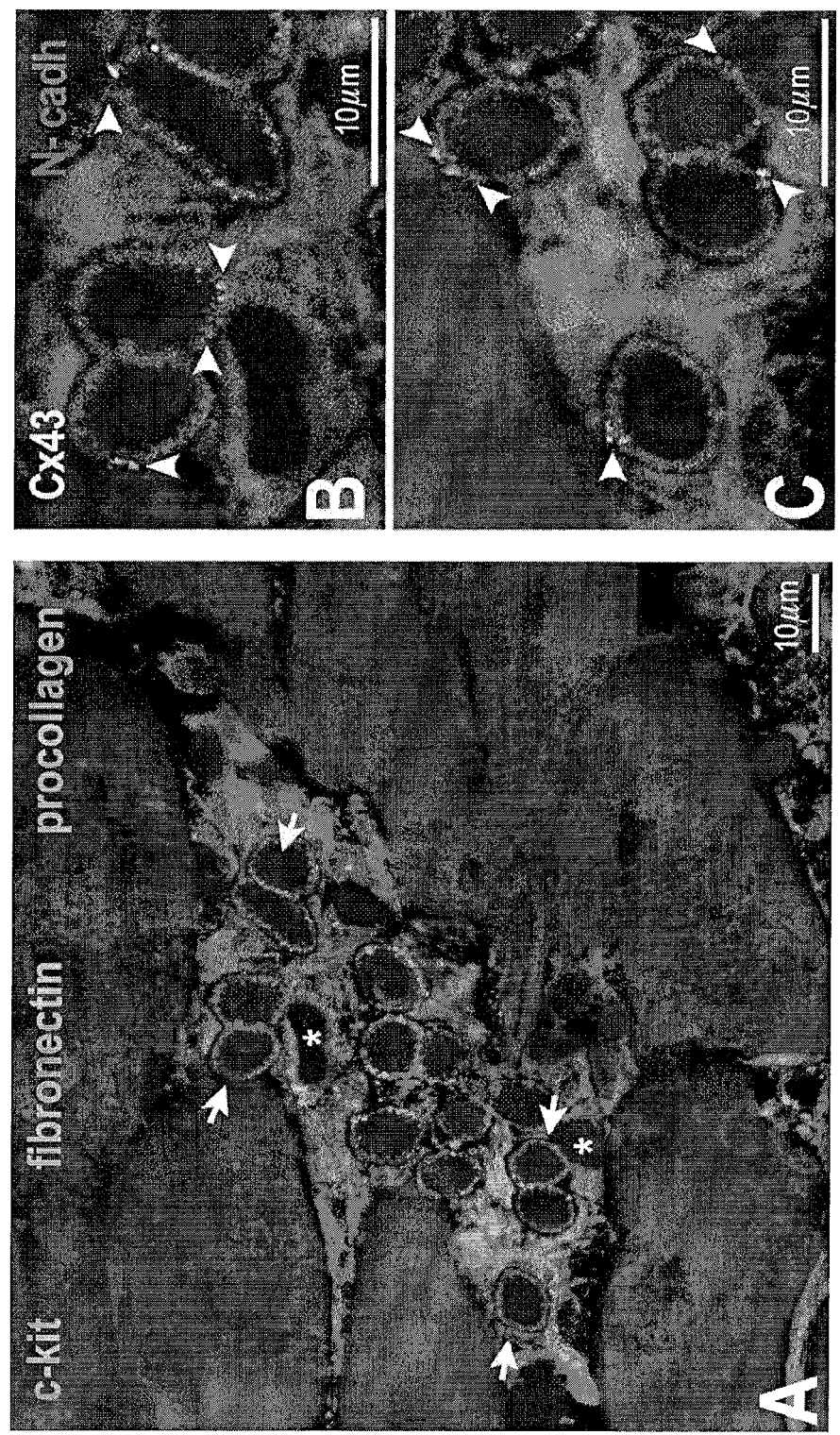
Figure 8A-C

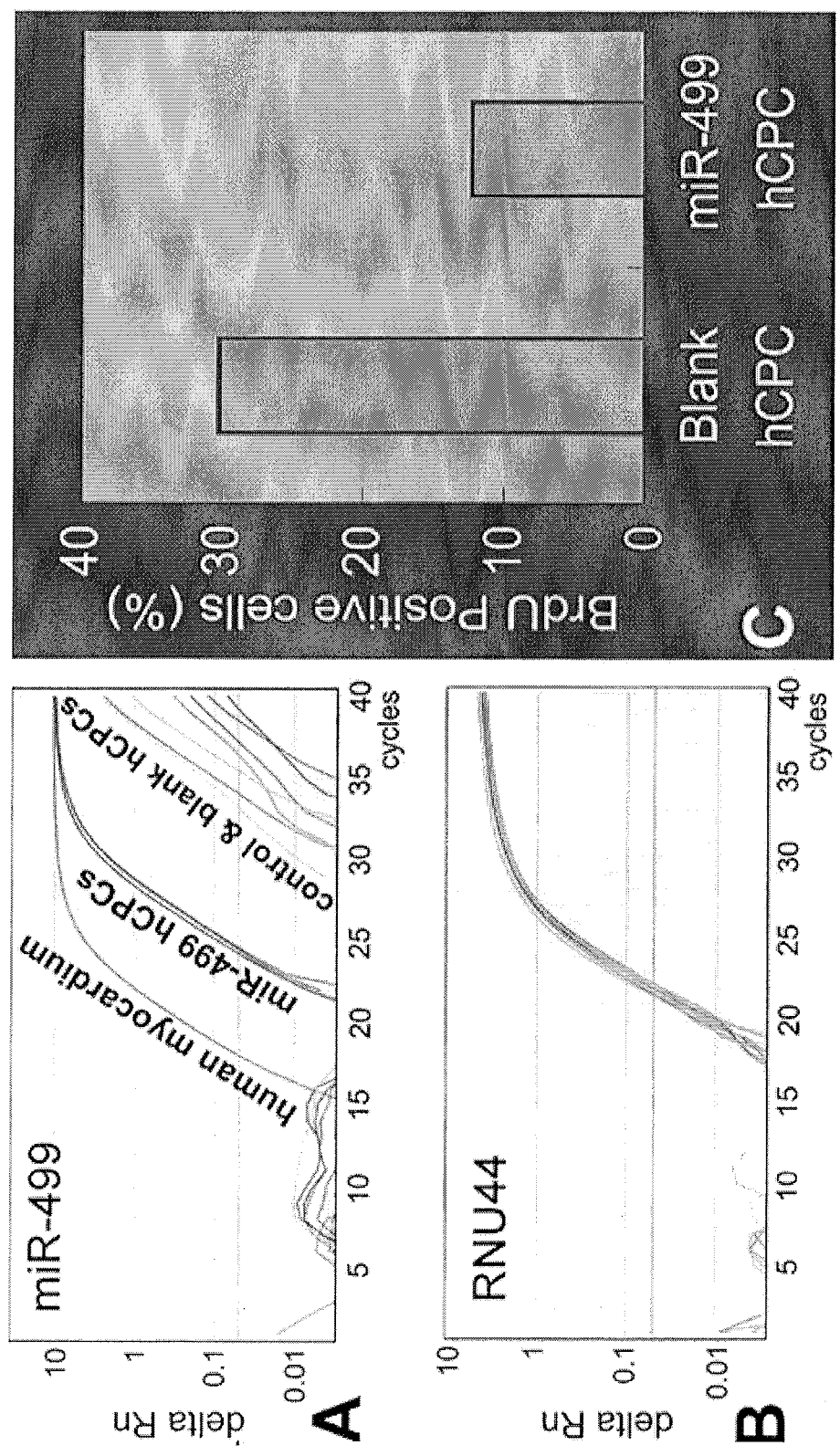
Figure 9A-C

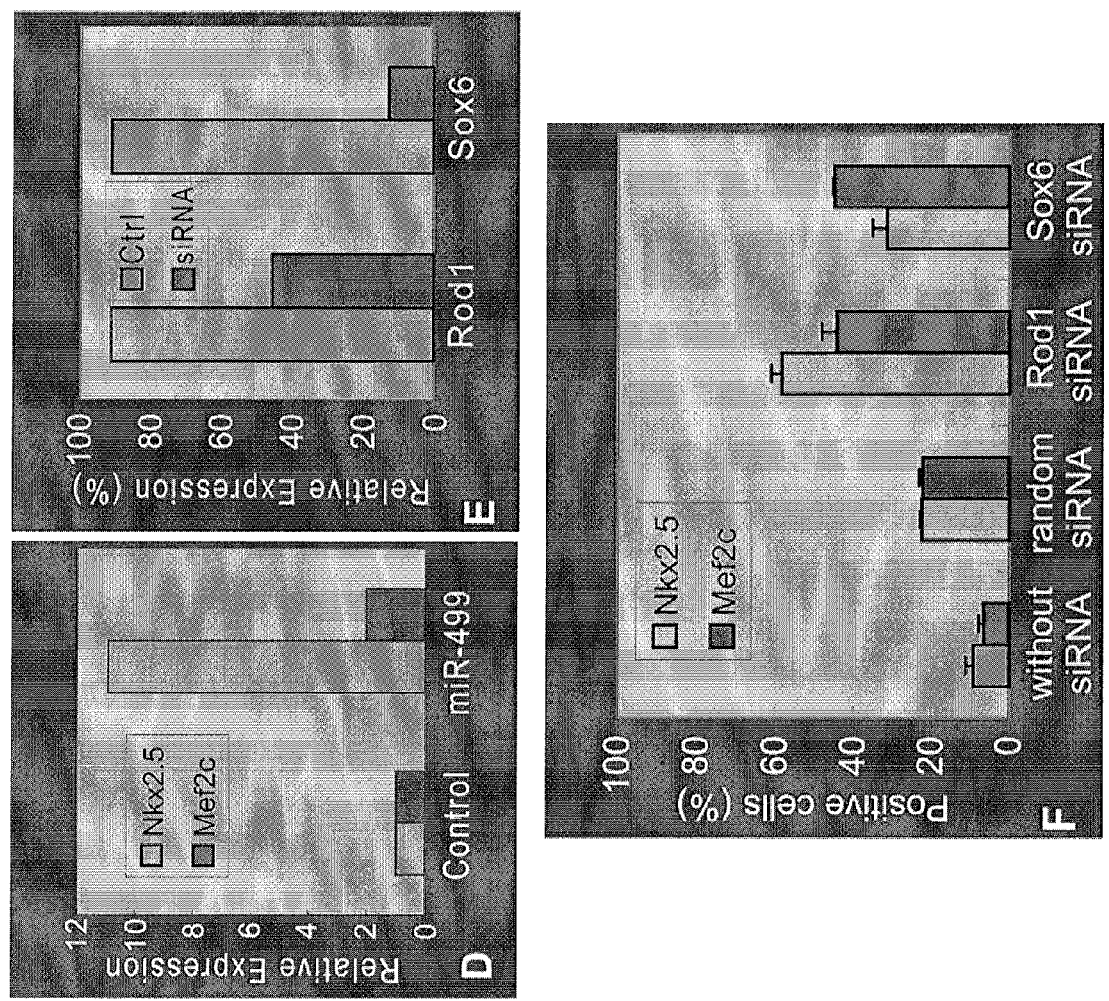
Figure 9D-F

SEQUENCE LISTING

```
<160> NUMBER OF SEQ ID NOS: 56

<210> SEQ ID NO 1
<211> LENGTH: 71
<212> TYPE: RNA
<213> ORGANISM: Homo sapiens

<400> SEQUENCE: 1
ugggaaacau acuucuuuau augcccauau ggaccugcua agcuauggaa uguaaagaag      60
uauguaucuc a                                                          71

<210> SEQ ID NO 2
<211> LENGTH: 85
<212> TYPE: RNA
<213> ORGANISM: Homo sapiens

<400> SEQUENCE: 2
accuacucag aguacauacu ucuuuaugua cccauaugaa cauacaaugc uaggaaugu       60 aaagaaguau guauuuuugg uaggc                                           85

<210> SEQ ID NO 3
<211> LENGTH: 22
<212> TYPE: RNA
<213> ORGANISM: Homo sapiens

<400> SEQUENCE: 3
uggaauguaa agaaguaugu au                                              22

<210> SEQ ID NO 4
<211> LENGTH: 122
<212> TYPE: RNA
<213> ORGANISM: Homo sapiens

<400> SEQUENCE: 4
gcccuguccc cugugccuug ggcgggcggc uguuaagacu ugcagugaug uuuaacuccu      60
cuccacguga acaucacagc aagucugugc ugcuucccgu cccuacgcug ccugggcagg    120
gu                                                                  122

<210> SEQ ID NO 5
<211> LENGTH: 21
<212> TYPE: RNA
<213> ORGANISM: Homo sapiens

<400> SEQUENCE: 5
uuaagacuug cagugauguu u                                              21

<210> SEQ ID NO 6
<211> LENGTH: 22
<212> TYPE: RNA
<213> ORGANISM: Homo sapiens

<400> SEQUENCE: 6
aacaucacag caagucugug cu                                              22

<210> SEQ ID NO 7
<211> LENGTH: 88
<212> TYPE: RNA
<213> ORGANISM: Homo sapiens
```

```
<400> SEQUENCE: 7
acaaugcuuu gcuagagcug guaaaaugga accaaaucgc cucuucaaug gauuuggucc    60
ccuucaacca gcuguagcua ugcauuga                                       88

<210> SEQ ID NO 8
<211> LENGTH: 102
<212> TYPE: RNA
<213> ORGANISM: Homo sapiens

<400> SEQUENCE: 8
gggagccaaa ugcuuugcua gagcugguaa aauggaacca aaucgacugu ccaauggauu    60 uggucccuu caaccagcug uagcugugca uugauggcgc cg                       102

<210> SEQ ID NO 9
<211> LENGTH: 22
<212> TYPE: RNA
<213> ORGANISM: Homo sapiens

<400> SEQUENCE: 9
uuuggucccc uucaaccagc ug                                             22

<210> SEQ ID NO 10
<211> LENGTH: 119
<212> TYPE: RNA
<213> ORGANISM: Homo sapiens

<400> SEQUENCE: 10
ccucagaaga aagaugcccc cugcucuggc uggucaaacg gaaccaaguc cgucuuccug    60
agagguuugg uccccuucaa ccagcuacag cagggcuggc aaugcccagu ccuuggaga   119

<210> SEQ ID NO 11
<211> LENGTH: 22
<212> TYPE: RNA
<213> ORGANISM: Homo sapiens

<400> SEQUENCE: 11
uuuggucccc uucaaccagc ua                                             22

<210> SEQ ID NO 12
<211> LENGTH: 33
<212> TYPE: DNA
<213> ORGANISM: Artificial Sequence
<220> FEATURE:
<223> OTHER INFORMATION: PCR primer

<400> SEQUENCE: 12
cctaaggatc ccacgccccc tacaggctgc cac                                 33

<210> SEQ ID NO 13
<211> LENGTH: 31
<212> TYPE: DNA
<213> ORGANISM: Artificial Sequence
<220> FEATURE:
<223> OTHER INFORMATION: PCR primer

<400> SEQUENCE: 13
acctaaagct tcaccgcccc cccaccccca g                                   31

<210> SEQ ID NO 14
<211> LENGTH: 36
<212> TYPE: DNA
<213> ORGANISM: Artificial Sequence
```

```
<220> FEATURE:
<223> OTHER INFORMATION: PCR primer

<400> SEQUENCE: 14
tgtttgacgc gttaaaacac tctgacattt cgctcc                              36

<210> SEQ ID NO 15
<211> LENGTH: 36
<212> TYPE: DNA
<213> ORGANISM: Artificial Sequence
<220> FEATURE:
<223> OTHER INFORMATION: PCR primer

<400> SEQUENCE: 15
agtcctgttt aaacttctct ttatcactat ccagag                              36

<210> SEQ ID NO 16
<211> LENGTH: 35
<212> TYPE: DNA
<213> ORGANISM: Artificial Sequence
<220> FEATURE:
<223> OTHER INFORMATION: PCR primer

<400> SEQUENCE: 16
tgacctacgc gtgaaattgt ctccttatac tggac                               35

<210> SEQ ID NO 17
<211> LENGTH: 41
<212> TYPE: DNA
<213> ORGANISM: Artificial Sequence
<220> FEATURE:
<223> OTHER INFORMATION: PCR primer

<400> SEQUENCE: 17 aaagggttt aaacaatgct atatgtgtta ggaaagagg c                          41

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
aggcgattaa gttgggta                                                  18

<210> SEQ ID NO 19
<211> LENGTH: 35
<212> TYPE: DNA
<213> ORGANISM: Artificial Sequence
<220> FEATURE:
<223> OTHER INFORMATION: PCR primer

<400> SEQUENCE: 19
ataagggccg gcagactgtg gtgagccgag gactt                               35

<210> SEQ ID NO 20
<211> LENGTH: 31
<212> TYPE: DNA
<213> ORGANISM: Artificial Sequence
<220> FEATURE:
<223> OTHER INFORMATION: PCR primer

<400> SEQUENCE: 20
tttcttttta aaaattgtag cacagaacaa c                                   31
```

```
<210> SEQ ID NO 21
<211> LENGTH: 28
<212> TYPE: DNA
<213> ORGANISM: Artificial Sequence
<220> FEATURE:
<223> OTHER INFORMATION: PCR primer

<400> SEQUENCE: 21
tttagaagct ttggactcac ttgacagg                                    28

<210> SEQ ID NO 22
<211> LENGTH: 29
<212> TYPE: DNA
<213> ORGANISM: Artificial Sequence
<220> FEATURE:
<223> OTHER INFORMATION: PCR primer

<400> SEQUENCE: 22
gttaggaatt ctttaagtcc taaggtcac                                   29

<210> SEQ ID NO 23
<211> LENGTH: 28
<212> TYPE: DNA
<213> ORGANISM: Artificial Sequence
<220> FEATURE:
<223> OTHER INFORMATION: PCR primer

<400> SEQUENCE: 23
atggtaagct tcaaggacat gaaaggtt                                    28

<210> SEQ ID NO 24
<211> LENGTH: 29
<212> TYPE: DNA
<213> ORGANISM: Artificial Sequence
<220> FEATURE:
<223> OTHER INFORMATION: PCR primer

<400> SEQUENCE: 24
tacttgaatt cagcaaacaa aaactcctc                                   29

<210> SEQ ID NO 25
<211> LENGTH: 28
<212> TYPE: DNA
<213> ORGANISM: Artificial Sequence
<220> FEATURE:
<223> OTHER INFORMATION: PCR primer

<400> SEQUENCE: 25
agccaaagct tgcttgtccc cggaaccg                                    28

<210> SEQ ID NO 26
<211> LENGTH: 31
<212> TYPE: DNA
<213> ORGANISM: Artificial Sequence
<220> FEATURE:
<223> OTHER INFORMATION: PCR primer

<400> SEQUENCE: 26
gagaagaatt cacagaaaag tcagattgta g                                31

<210> SEQ ID NO 27
<211> LENGTH: 21
<212> TYPE: DNA
<213> ORGANISM: Homo sapiens

<400> SEQUENCE: 27 agcttttgc catccaccag g                                            21
```

```
<210> SEQ ID NO 28
<211> LENGTH: 21
<212> TYPE: DNA
<213> ORGANISM: Homo sapiens

<400> SEQUENCE: 28
ataacaggca tcccaggctc t                                              21

<210> SEQ ID NO 29
<211> LENGTH: 22
<212> TYPE: DNA
<213> ORGANISM: Homo sapiens

<400> SEQUENCE: 29
ccgacatgca taactccaac at                                             22

<210> SEQ ID NO 30
<211> LENGTH: 24
<212> TYPE: DNA
<213> ORGANISM: Homo sapiens

<400> SEQUENCE: 30
cggtcggggt ttgtatttat agtt                                           24

<210> SEQ ID NO 31
<211> LENGTH: 23
<212> TYPE: DNA
<213> ORGANISM: Homo sapiens

<400> SEQUENCE: 31
gtccaaacat caagcagtac agc                                            23

<210> SEQ ID NO 32
<211> LENGTH: 24
<212> TYPE: DNA
<213> ORGANISM: Homo sapiens

<400> SEQUENCE: 32
agatcatcca ctgtaacaga aggg                                           24

<210> SEQ ID NO 33
<211> LENGTH: 21
<212> TYPE: DNA
<213> ORGANISM: Homo sapiens

<400> SEQUENCE: 33
tctatccacg tgcctacagc g                                              21

<210> SEQ ID NO 34
<211> LENGTH: 21
<212> TYPE: DNA
<213> ORGANISM: Homo sapiens

<400> SEQUENCE: 34
gctccagctc atagacctgc g                                              21

<210> SEQ ID NO 35
<211> LENGTH: 24
<212> TYPE: DNA
<213> ORGANISM: Homo sapiens

<400> SEQUENCE: 35
tggtgtaaca catcgacctc caag                                           24
```

<210> SEQ ID NO 36
<211> LENGTH: 24
<212> TYPE: DNA
<213> ORGANISM: Homo sapiens

<400> SEQUENCE: 36
tcaagttacc aggtgagacc agca                                    24

<210> SEQ ID NO 37
<211> LENGTH: 21
<212> TYPE: DNA
<213> ORGANISM: Homo sapiens

<400> SEQUENCE: 37
ggagatgcgt cccatcaaga c                                       21

<210> SEQ ID NO 38
<211> LENGTH: 20
<212> TYPE: DNA
<213> ORGANISM: Homo sapiens

<400> SEQUENCE: 38
ggagacgcat agccttgtgg                                         20

<210> SEQ ID NO 39
<211> LENGTH: 20
<212> TYPE: DNA
<213> ORGANISM: Homo sapiens

<400> SEQUENCE: 39
agaagggcac agggtctcct                                         20

<210> SEQ ID NO 40
<211> LENGTH: 20
<212> TYPE: DNA
<213> ORGANISM: Homo sapiens

<400> SEQUENCE: 40
actccgggtc atttgctgct                                         20

<210> SEQ ID NO 41
<211> LENGTH: 25
<212> TYPE: DNA
<213> ORGANISM: Homo sapiens

<400> SEQUENCE: 41
aagatcaaga tcattgctcc tcctg                                   25

<210> SEQ ID NO 42
<211> LENGTH: 21
<212> TYPE: DNA
<213> ORGANISM: Homo sapiens

<400> SEQUENCE: 42
cggactcgtc atactcctgc t                                       21

<210> SEQ ID NO 43
<211> LENGTH: 33
<212> TYPE: DNA
<213> ORGANISM: Artificial Sequence
<220> FEATURE:
<223> OTHER INFORMATION: PCR primer

<400> SEQUENCE: 43
caagggaatt ccccatctgg gagacagacc ctc                    33

<210> SEQ ID NO 44
<211> LENGTH: 33
<212> TYPE: DNA
<213> ORGANISM: Artificial Sequence
<220> FEATURE:
<223> OTHER INFORMATION: PCR primer

<400> SEQUENCE: 44
gatgggaatt ccttcgctgt ctcccatcac cac                    33

<210> SEQ ID NO 45
<211> LENGTH: 32
<212> TYPE: DNA
<213> ORGANISM: Artificial Sequence
<220> FEATURE:
<223> OTHER INFORMATION: PCR primer

<400> SEQUENCE: 45
gacgggaatt cacgtagaaa gaagcaagag ct                     32

<210> SEQ ID NO 46
<211> LENGTH: 31
<212> TYPE: DNA
<213> ORGANISM: Artificial Sequence
<220> FEATURE:
<223> OTHER INFORMATION: PCR primer

<400> SEQUENCE: 46
cagaattcta cattagtaag ctgaatgttt c                      31

<210> SEQ ID NO 47
<211> LENGTH: 34
<212> TYPE: DNA
<213> ORGANISM: Artificial Sequence
<220> FEATURE:
<223> OTHER INFORMATION: PCR primer

<400> SEQUENCE: 47
gaagcgaatt ctccatcggg actgcttggt ggag                   34

<210> SEQ ID NO 48
<211> LENGTH: 33
<212> TYPE: DNA
<213> ORGANISM: Artificial Sequence
<220> FEATURE:
<223> OTHER INFORMATION: PCR primer

<400> SEQUENCE: 48
ctcaggaatt cacttacttg gagctgacca cgt                    33

<210> SEQ ID NO 49
<211> LENGTH: 33
<212> TYPE: DNA
<213> ORGANISM: Artificial Sequence
<220> FEATURE:
<223> OTHER INFORMATION: PCR primer

<400> SEQUENCE: 49
aatgcgaatt cttttttgcat tacaggctta gac                   33

<210> SEQ ID NO 50
<211> LENGTH: 33
<212> TYPE: DNA
<213> ORGANISM: Artificial Sequence -continued

```
<220> FEATURE:
<223> OTHER INFORMATION: PCR primer

<400> SEQUENCE: 50
tctctgaatt cctgggagca taagaatatg gtg                      33

<210> SEQ ID NO 51
<211> LENGTH: 21
<212> TYPE: RNA
<213> ORGANISM: Homo sapiens

<400> SEQUENCE: 51
uacuuuaacu guuagucuua a                                   21

<210> SEQ ID NO 52
<211> LENGTH: 21
<212> TYPE: RNA
<213> ORGANISM: Homo sapiens

<400> SEQUENCE: 52
aaaaaaaguu uacagucuua a                                   21

<210> SEQ ID NO 53
<211> LENGTH: 21
<212> TYPE: RNA
<213> ORGANISM: Homo sapiens

<400> SEQUENCE: 53
ugccuucuuc aguagucuua a                                   21

<210> SEQ ID NO 54
<211> LENGTH: 21
<212> TYPE: RNA
<213> ORGANISM: Homo sapiens

<400> SEQUENCE: 54
uagaugucuu acaagucuua u                                   21

<210> SEQ ID NO 55
<211> LENGTH: 21
<212> TYPE: RNA
<213> ORGANISM: Homo sapiens

<400> SEQUENCE: 55
uuaauauuuu gaaagucuua a                                   21

<210> SEQ ID NO 56
<211> LENGTH: 21
<212> TYPE: RNA
<213> ORGANISM: Homo sapiens

<400> SEQUENCE: 56
ggagacacug caaagucuua g                                   21
```

COMPOSITIONS COMPRISING CARDIAC STEM CELLS OVEREXPRESSING SPECIFIC MICRORNAS AND METHODS OF THEIR USE IN REPAIRING DAMAGED MYOCARDIUM

CROSS-REFERENCE TO RELATED APPLICATIONS

This application is a continuation of U.S. patent application Ser. No. 12/480,861, filed Jun. 9, 2009, which claims the benefit of U.S. Provisional Application Ser. No. 61/059,936, filed Jun. 9, 2008, both of which are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AUTL00702US_SeqList_ST25.txt, date recorded: Sep. 18, 2012, file size 10 kilobytes).

FIELD OF THE INVENTION

The present invention relates generally to the field of cardiology, and more particularly relates to compositions of cardiac stem cells overexpressing specific microRNAs and their use for promoting stem cell differentiation. The invention also relates to methods of using the compositions comprising microRNA-overexpressing cardiac stem cells for repairing damaged myocardium.

BACKGROUND OF THE INVENTION

Cardiovascular disease is a major health risk throughout the industrialized world. An estimated 80.7 million Americans suffer from one or more types of cardiovascular disease, including high blood pressure, coronary heart disease, heart failure, and stroke (Heart Disease and Stroke Statistics, American Heart Association, 2008). Cardiovascular disease was the cause of 57 percent of the deaths in 2004, and every year since 1900 (except 1918), cardiovascular disease accounts for more deaths than any other single cause or group of causes in the United States.

One of the most well-known types of cardiovascular disease is myocardial infarction (MI), commonly known as a heart attack. Estimates for 2005 show that 8.1 million people in the United States suffer from MI (Heart Disease and Stroke Statistics, American. Heart Association, 2008). MI is caused by a sudden and sustained lack of blood flow to an area of the heart, typically caused by narrowing of a coronary artery. Without adequate blood supply, the tissue becomes ischemic, leading to the death of myocytes and vascular structures. This area of necrotic tissue is referred to as the infarct site, and will eventually become scar tissue. Survival is dependent on the size of this infarct site, with the probability of recovery decreasing with increasing infarct size. For example, in humans, an infarct of 46% or more of the left ventricle triggers irreversible cardiogenic shock and death.

Myocardial regeneration involves the replacement of cells lost following injury, such as an ischemic injury. Damage creates a barrier to restitutio ad integrum and promotes the initiation of a healing process that leads to scar formation (Leri et al. 2005). However, the scar does not possess the biochemical, physical and functional properties of the original tissue. Effective cardiac repair necessitates creating myocardium de novo that closely resembles the morphology of the normal adult heart.

Successful regeneration of myocardial tissue after acute infarction has been achieved by employing cardiac stem cells (CSCs). Administration of autologous CSCs to the damaged myocardium or local activation of resident CSCs by intramyocardial administration of growth factors results in a significant recovery of ventricular muscle mass. However, the regenerated myocytes are small and have the characteristics of fetal-neonatal cells (Beltrami et al., 2003; Urbanek et al., 2005; Linke et al., 2005; and Bearzi et al. 2007). Thus, one of the major problems in cardiac repair is the lack of maturation of the newly formed cardiomyocytes. This problem is even more apparent when bone marrow progenitor cells (BMPCs) are employed for myocardial repair. Mobilization of BMPCs with cytokines or direct implantation of BMPCs in proximity of an infarct typically shows BMPC transdifferentiation with the generation of a large number of immature cardiomyocytes. Unfortunately, these cells rarely increase in size over time and fail to attain the properties of fully developed adult myocytes.

Thus, it is desirable to develop methods of facilitating the differentiation of CSCs and BMPCs into fully mature cardiomyocytes. Such methods would significantly improve stem cell-mediated treatment of myocardial infarctions and provide new approaches to the management of human heart failure.

SUMMARY OF THE INVENTION

The present invention provides compositions of modified stem cells that are capable of differentiating into cardiomyocytes that attain the fully mature, adult phenotype. Such compositions are useful in the treatment of various cardiovascular disorders that result in damaged heart tissue. Modified stem cells of the invention comprise a transgene that affects the expression of at least one gene that inhibits or promotes cardiomyogenesis.

The modified stem cells of the invention are adult cardiac stem cells or adult bone marrow progenitor cells that comprise a transgene. Preferably, the stem cells of the invention are lineage negative and c-kit positive. The stem cells may be human stem cells.

In particular, the present invention provides pharmaceutical compositions comprising an effective amount of modified stem cells and a pharmaceutically acceptable carrier. In one embodiment, the composition comprises cardiac stem cells and a pharmaceutically acceptable carrier, wherein said cardiac stem cells comprise a transgene. In another embodiment, said transgene encodes a microRNA. The microRNA may be a microRNA that is abundantly expressed in adult cardiomyocytes. In a preferred embodiment, the transgene encodes miR-499.

In another embodiment, the cardiac stem cells comprise a transgene that encodes an inhibitory RNA molecule, such as siRNA, shRNA, or antisense. The inhibitory RNA molecule preferably comprises a nucleic acid sequence that is substantially complementary to a polynucleotide sequence encoding a protein that inhibits cardiomyogenesis. In some embodiments, the inhibitory RNA molecule targets a polynucleotide sequence encoding a protein selected from the group consisting of Sox5, Sox6 and Rod1.

The present invention also contemplates pharmaceutical compositions comprising modified cardiac stem cells and vascular progenitor cells. Vascular progenitor cells (VPCs) are a specific subset of cardiac stem cells that are c-kit and flk1 positive. VPCs may differentiate into endothelial cells and smooth muscles, thereby forming new vascular structures.

The invention also provides methods for regenerating damaged myocardium in a subject in need thereof. In one embodiment, the method comprises administering a pharmaceutical composition of the invention to an area of damaged myocardium in the subject, wherein the cardiac stem cells differentiate into mature, functional cardiomyocytes following administration, thereby regenerating the damaged myocardium. In preferred embodiments, the regenerated myocardium exhibits the functional characteristics of adult myocardium. In another preferred embodiment, the cardiac stem cells are autologous or isolated from the same subject to which they are re-administered.

In another embodiment, the method comprises extracting cardiac stem cells from the subject; incorporating a transgene into said extracted cardiac stem cells, wherein said transgene encodes a microRNA; and administering the cardiac stem cells comprising the transgene to an area of damaged myocardium in the subject, wherein the cardiac stem cells differentiate into mature, functional cardiomyocytes following administration, thereby regenerating the damaged myocardium. In a preferred embodiment, the cardiac stem cells overexpress miR-499. In some embodiments, the method further comprises administering vascular progenitor cells to the area of damaged myocardium.

In another embodiment of the invention, the method comprises administering unmodified cardiac stem cells to an area of damaged myocardium in a subject in need thereof, wherein the cardiac stem cells differentiate into myocytes, smooth muscle cells, and endothelial cells after their administration, thereby regenerating the damaged myocardium; and administering a transgene encoding a microRNA to the area of regenerated myocardium, wherein the regenerated myocardium exhibits the functional characteristics of adult myocardium following transgene administration.

BRIEF DESCRIPTION OF THE DRAWINGS

FIG. 9. miR-499 and CSC proliferation and differentiation. A, B. Quantitative RT-PCR of miR-499 in human myocardium and hCSCs overexpressing miR-499. Non-transfected hCSCs (control) and hCSCs transfected with an empty vector (blank) were employed as control. Reaction was normalized with human small nucleolar RNA, RNU44. C. BrdU incorporation is higher in hCSCs transfected with an empty vector (Blank) than in hCSCs overexpressing miR-499. D. Quantitative RT-PCR of Nkx2.5 and Mef2C mRNA in hCSCs transfected with miR-499 expression vector. E. Downregulation of Rod1 and Sox6 transcripts following CSC transfection with Rod1-siRNA and Sox6-siRNA, respectively. F. Activation of differentiation of CSCs by Rod1-siRNA and Sox6-siRNA.

DETAILED DESCRIPTION OF THE INVENTION

Figure 1:
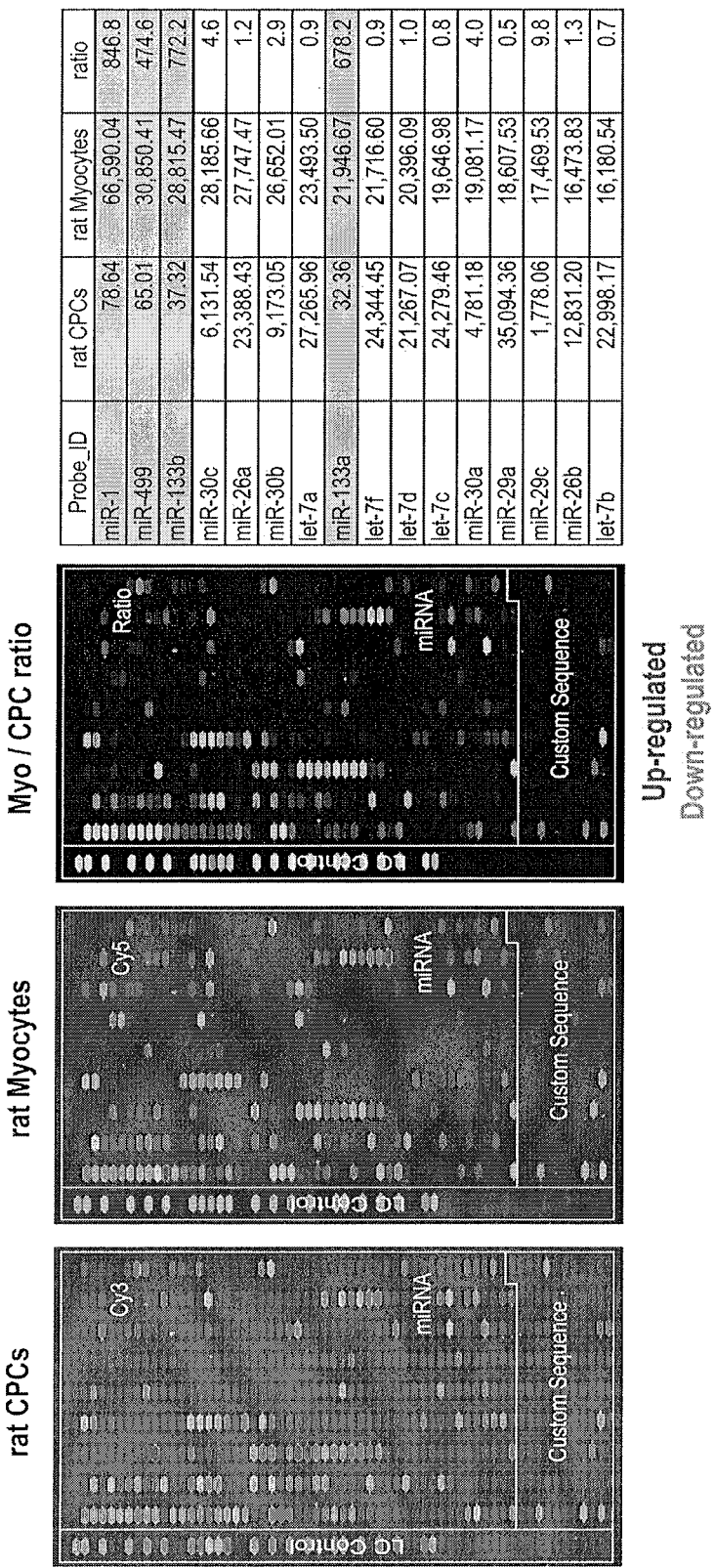
FIG. 1. MiR hybridization array comparing the level of expression of distinct miRs in CSCs and myocytes obtained from the rat heart.

As used herein, "autologous" refers to something that is derived or transferred from the same individual's body (i.e., autologous blood donation; an autologous bone marrow transplant).

As used herein, "allogenic" refers to something that is genetically different although belonging to or obtained from the same species (e.g., allogeneic tissue grafts or organ transplants).

As used herein, "stem cells" are used interchangeably with "progenitor cells" and refer to cells that have the ability to renew themselves through mitosis as well as differentiate into various specialized cell types. The stem cells used in the invention are somatic stem cells, such as bone marrow or cardiac stem cells or progenitor cells. "Vascular progenitor cells" or VPCs are a subset of adult cardiac stem cells that are c-kit positive and flk1 positive, which generate predominantly endothelial cells and smooth muscle cells. "Myocyte progenitor cells" or MPCs are a subset of adult cardiac stem cells that are c-kit positive and flk1 negative, which generate cardiomyocytes predominantly.

As used herein, "adult" stem cells refers to stem cells that are not embryonic in origin nor derived from embryos or fetal tissue.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

As used herein, the term "transgene" refers to a polynucleotide sequence that is not endogenously expressed in a host cell. The polynucleotide sequence may produce RNA or protein upon introduction into the host cell. Alternatively, the polynucleotide sequence may alter the normal gene expression of the host cell into which it is introduced.

As used herein, the term "cytokine" is used interchangeably with "growth factor" and refers to peptides or proteins that bind receptors on cell surfaces and initiate signaling cascades thus influencing cellular processes. The terms "cytokine" and "growth factor" encompass functional variants of the native cytokine or growth factor. A functional variant of the cytokine or growth factor would retain the ability to activate its corresponding receptor. Variants can include amino acid substitutions, insertions, deletions, alternative splice variants, or fragments of the native protein. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological activity can be found using computer programs well known in the art, for example, DNASTAR software.

As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein, "patient" or "subject" may encompass any vertebrate including but not limited to humans, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like.

The pharmaceutical compositions of the present invention may be used as therapeutic agents—i.e. in therapy applications. As herein, the terms "treatment" and "therapy" include curative effects, alleviation effects, and prophylactic effects. In certain embodiments, a therapeutically effective dose of progenitor cells is applied, delivered, or administered to the heart or implanted into the heart. An effective dose or amount is an amount sufficient to effect a beneficial or desired clinical result. Said dose could be administered in one or more administrations.

Mention is made of the following related pending patent applications:

U.S. Application Publication No. 2003/0054973, filed Jun. 5, 2002, which is herein incorporated by reference in its entirety, discloses methods, compositions, and kits for repairing damaged myocardium and/or myocardial cells including the administration cytokines.

U.S. Application Publication No. 2006/0239983, filed Feb. 16, 2006, which is herein incorporated by reference in its entirety, discloses methods, compositions, and kits for repairing damaged myocardium and/or myocardial cells including the administration of cytokines and/or adult stem cells as well as methods and compositions for the development of large arteries and vessels. The application also discloses methods and media for the growth, expansion, and activation of human cardiac stem cells.

U.S. Provisional Application No. 60/991,515, filed Nov. 30, 2007, which is herein incorporated by reference in its entirety, discloses compositions comprising vascular progenitor cells (VPCs) and myocyte progenitor cells (MPCs), both of which are distinct subsets of adult cardiac stem cells. The application also discloses methods of using the different compositions for repairing damaged myocardium and generating coronary vasculature.

The adult heart is largely composed of terminally differentiated myocytes. Damaged and old units of this highly specialized compartment of contracting cells are constantly replaced by new younger elements. The heart is, in fact, a dynamic organ where myocyte death and growth are tightly regulated to maintain physiologic homeostasis (Anversa et al., 1998; Anversa et al., 2002; and Anversa et al., 2006). Mitosis and cytokinesis have been recognized mostly in small poorly differentiated cells with a thin sub-sarcolemmal halo of myofibrils (Kajstura et al., 1998; Beltrami et al., 2001; and Limana et al., 2002). Typically, these dividing myocytes are less than 150 $\mu m^2$ in cross-sectional area and display telomerase activity (Urbanek et al., 2003; and Urbanek et al., 2005a). The observation that cycling myocytes are smaller than mature myocytes suggest that newly formed cells do not derive from pre-existing myocytes but from activation, replication and differentiation of resident cardiac progenitor cells (CPCs), also referred to as cardiac stem cells (CSCs) (Beltrami et al., 2003; Oh et al., 2003; Pfister et al., 2005; Urbanek et 2005b; Linke et al., 2005; Smith et al., 2007; and Bearzi et al., 2007). Thus, the heart contains two groups of myocytes: a large fraction of terminally differentiated cells and a small fraction of dividing cells. The latter is consistent with the presence of a compartment of amplifying myocytes derived from the activation and growth of CSCs.

When a stem cell divides, two daughter cells are formed; they may maintain stem cell properties or become early committed amplifying cells (Götz and Huttner, 2005; and Morrison and Kimble, 2006). Transit amplifying cells proliferate and simultaneously differentiate (Watt, 1998; Jones and Watt, 1993; Watt and Hogan, 2000; Taylor et al., 2000; and Wright, 2000). Telomerase activity is one of the critical determinants of the number of rounds of division and rate of differentiation of amplifying cells (Lansdorp, 2005; and Flores et al., 2006). When telomerase activity is downregulated, cell replication is attenuated and cell maturation takes place leading to the acquisition of the adult phenotype. In the intact heart, the loss of stemness is accompanied by lineage commitment and the generation of terminally differentiated cardiomyocytes. However, in spite of this remarkable growth reserve, CSCs do not behave in a similar manner following extensive myocardial injury; spontaneous (Beltrami et al., 2001; Urbanek et al., 2003; and Urbanek et al., 2005a) or induced (Beltrami et al., 2003; Urbanek et al., 2005b; Linke et al., 2005; and Bearzi et al., 2007 9, 12, 13, 15) myocardial regeneration does not recapitulate tissue homeostasis failing to restore the structural and functional integrity of the organ.

Local activation of resident cardiac stem cells (CSCs) by growth factors acutely after infarction results in a significant recovery of ventricular muscle mass. However, only 20% of the regenerated myocytes acquire the adult phenotype over a period of 4 months while the vast majority of cells display fetal-neonatal characteristics. Similarly, the intramyocardial injection of CSCs induces a substantial restoration of the infarct but, also in this case, the newly formed myocytes are small and resemble fetal-neonatal cells. In contrast, the occasional migration of CSCs or bone marrow progenitor cells (BMPCs) from the border zone to the remote myocardium results in the formation of myocytes which are indistinguishable from the preexisting adjacent cardiomyocytes. Therefore, the phenotype and organization of regenerated myocytes in the infarcted region differ strikingly from those of newly formed myocytes located in the distant non-infarcted myocardium. Efficient cardiac repair requires that the regenerated myocardium closely resemble the morphology and function of the mature adult heart. Thus, CSCs that can differentiate into fully mature, functional cardiomyocytes will greatly improve the repair of damaged or infarcted myocardial tissue.

The inventors of the present invention have discovered methods of facilitating the differentiation of CSCs into cardiomyocytes that can achieve the fully mature, adult phenotype. Accordingly, the present invention provides compositions comprising modified CSCs that have the ability to generate mature, functional cardioymyocytes, and methods of using the inventive compositions to repair damaged myocardium in a subject in need thereof.

The inventors have surprisingly found that regulating a specific subset of genes in isolated CSCs can promote the differentiation of the CSCs into cardiomyocytes. Moreover, the differentiated cardiomyocytes are able to achieve the mature phenotype of adult cardiomyocytes unlike cardiomyocytes produced from unmodified or natural CSCs. Thus, the present invention provides compositions comprising "modified CSCs" that have the ability to give rise to fully mature, functional cardiomyocytes. "Modified CSCs", as used herein, refers to CSCs comprising a transgene, which affects the expression of at least one gene that inhibits or promotes cardiomyogenesis.

The present invention is related to modified adult stem cells or progenitor cells, wherein the stem cells comprise a transgene. Preferably the adult stem cells are cardiac stem cells (CSCs) or bone marrow progenitor cells (BMPCs). In some embodiments, the stem cells are human stem cells. In preferred embodiments, the stem cells are human cardiac stem cells. Methods of isolating adult stem cells are known in the art. Stem cells may be isolated from tissue specimens, such as myocardium or bone marrow, obtained from a subject or patient. By way of example, the tissue specimens may be minced and placed in appropriate culture medium. Stem cells growing out from the tissue specimens can be observed in approximately 1-2 weeks after initial culture. At approximately 4 weeks after the initial culture, the expanded stem cells may be collected by centrifugation. U.S. Patent Application Publication No. 2006/0239983, filed Feb. 16, 2006, which is herein incorporated by reference, describes media appropriate for culturing and expanding adult stem cells. However, one of ordinary skill in the art would be able to determine the necessary components and modify commonly used cell culture media to be employed in culturing the isolated stem cells of the invention.

It is preferable that the stem cells of the invention are lineage negative (LinNEG). LinNEG stem cells can be isolated by various means, including but not limited to, removing lineage positive cells by contacting the stem cell population with antibodies against lineage markers and subsequently isolating the antibody-bound cells by using an anti-immunoglobulin antibody conjugated to magnetic beads and a biomagnet. Alternatively, the antibody-bound lineage positive stem cells may be retained on a column containing beads conjugated to anti-immunoglobulin antibodies.

The LinNEG stem cells preferably express one or more stem cell surface markers including c-kit, which is the receptor for stem cell factor, and multidrug resistance-1 (MDR1), which is a P-glycoprotein capable of extruding dyes, toxic substances and drugs from the cell. Positive selection methods for isolating a population of LinNEG stem cells expressing any one of these surface markers are well known to the skilled artisan. Examples of possible methods include, but are not limited to, various types of cell sorting, such as fluorescence activated cell sorting (FACS) and magnetic cell sorting as well as modified forms of affinity chromatography. In a preferred embodiment, the LinNEG stem cells are c-kit positive. In some embodiments, the cardiac stem cells may be further separated into vascular progenitor cells (VPCs) and myocyte progenitor cells (MPCs). VPCs are a subset of CSCs that co-express c-kit and flk1, and differentiate predominantly into endothelial cells and smooth muscle cells, thereby giving rise to vascular structures. MPCs are a subset of CSCs that are c-kit positive and flk1 negative, which generate cardiomyocytes predominantly. VPCs and MPCs are extensively described in co-pending U.S. Provisional Application No. 60/991,515, filed Nov. 30, 2007, which is herein incorporated by reference in its entirety.

The present invention provides compositions comprising modified stem cells, wherein said modified stem cells comprise a transgene. In one embodiment, the modified CSCs comprise a transgene encoding a microRNA. MicroRNAs (miRs) are small non-coding RNAs of about 18 to about 25 nucleotides in length that regulate gene expression by binding to messenger RNA (mRNA) and inhibiting translation of the mRNA into protein or promoting degradation of the mRNA. MiRs are derived from larger precursor molecules generated by the transcription of non-coding genes. These precursor molecules, termed primary miRNAs (pri-miRNAs), are generally several thousand bases long and transcribed by RNA polymerase II (pol II) from individual miRNA genes, from introns of protein coding genes, or from poly-cistronic transcripts that often encode multiple, closely related miRs. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miR. The mature miR strand is then incorporated into the RNA-induced silencing complex (RISC), where it associates with its target mRNAs by base-pair complementarity. In the relatively rare cases in which a miR base pairs perfectly with an mRNA target, it promotes mRNA degradation. More commonly, miRs form imperfect heteroduplexes with target mRNAs, inhibiting mRNA translation by binding to the 3'-untranslated region (UTR).

In some embodiments, the CSCs comprise a transgene that encodes a miR expressed in cardiomyocytes. Some non-limiting examples of miRs the are abundantly expressed in cardiomyocytes include miR-1, miR-499, miR-133a, miR-133b, miR-30a, miR-30b, miR-30c, miR-26a, miR-26b, miR-29a, miR-29c, let-7a, let-7b, let-7c, let-7d, and let-7f. In other embodiments, the CSCs comprise a transgene that encodes a miR that is differentially expressed in cardiomyoctes and unmodified or natural CSCs. MiRs that are differentially expressed include, but are not limited to, miR-1, miR-499, miR-133a, and miR-133b. In a preferred embodiment, the CSCs comprise a transgene encoding miR-499. MiR-499 is encoded within the $20^{th}$ intron of the Myh7b gene, which encodes a member of the sarcomeric myosin heavy chain (MHC) protein family. The miR-499 gene is in the same orientation as the Myh7b gene such that the two genes are co-transcribed. The Myh7b is expressed in brain, heart, skeletal muscle, and testis.

In another embodiment, the modified CSCs contain a transgene that encodes an inhibitory RNA molecule. "Inhibitory RNA molecules" include small interfering RNA molecules (siRNAs), short hairpin RNA molecules (shRNAs), and antisense oligonucleotides. siRNA molecules are double-stranded RNAs that are about 20 to about 25 nucleotides in length that inhibit gene expression of a target mRNA by initiating the RNA interference pathway. Similar to inhibition by miRs, one of the strands of the siRNA duplex is incorporated into the RISC complex, which binds to the target mRNA sequence and prevents translation of the mRNA or promotes mRNA degradation. shRNAs are single-stranded RNA molecules that contain regions of self-complementarity such that the molecule folds back on itself to form a double-stranded stem region and single-stranded loop region. shRNAs can also inhibit gene expression by entering the RNA interference pathway. For both siRNAs and shRNAs, the double-stranded regions must comprise a sequence that is substantially complementary to a target polynucleotide sequence. "Substantially complementary" refers to a sequence that is sufficiently complementary to a target polynucleotide sequence such that RNA interference is induced. The double-stranded regions of the siRNA or shRNA molecules may comprise a sequence that is at least about 75%, 80%, 85%, 90%, 95%, 96%, 97%, 98%, or 99% complementary to a target polynucleotide sequence. In some embodiments, the double-stranded regions of the siRNA or shRNA molecules may contain sequences that are 100% complementary to the target polynucleotide sequence.

The inhibitory molecules may also be antisense oligonucleotides. Antisense oligonucleotides are single stranded oligonucleotides that are substantially complementary to a target polynucleotide sequence. The antisense oligonucleotide inhibits gene expression by binding to complementary sequences in target mRNA molecules, thus preventing the protein synthesis machinery from accessing and translating the mRNA. Preferably the antisense oligonucleotides contain one or more chemical modifications including, but not limited to, locked nucleic acids, 2'-O-methyl, 2'-O-methoxyethyl, and 2'-fluoro sugar modifications; and one or more phosphorothioate linkages. The antisense oligonucleotide may comprise a sequence that is greater than about 90% complementary to a target polynucleotide sequence, such as about 91, 92, 93, 94, 95, 96, 97, 98, 99, or 100% complementary. The antisense oligonucleotide may be from about 50 nucleotides to about 500 nucleotides in length.

In some embodiments, the inhibitory RNA molecules are targeted to genes encoding proteins that inhibit differentiation of stem cells, and in particular proteins that inhibit cardiomyogenesis. Some non-limiting examples of proteins known to inhibit cardiomyogenesis include the SoxD family of proteins (e.g. Sox5 and Sox6), Wnt3a, Frz8, LRP6, p38 MAPK, Noggin, Ouabain, FOXO1, myostatin, and regulator of differentiation 1 (Rod1). Other suitable target genes include genes that function to preserve "stemness" in cardiac stem cells and inhibit their differentiation. Such genes include, but are not limited to SoxB1 proteins, Nanog, Oct 4, ETS1, and YES1. Other possible target genes include GATA 4, LIN28B, PAK7, heterogeneous nuclear ribonucleoprotein C (hnRNP C1/C2), YBX1, POU4F2, ARID2, WTAP, ENPP2, PFTK1, arginine decarboxylase (ADC), insulin receptor substrate 2 (IRS2), myristoylated alanine-rich protein kinase C substrate (MARCKS), mitogen-activated protein kinase 8 interacting protein 3 (MAPK8IP3), MAPK6, polypyrimidine tract binding protein 2 (PTBP2), CNOT6L, MYB, casein kinase 1 gamma 1 (CSNK1G1), SOX11, frizzled homolog 8 (FZD8), TSPAN12, phosphodiesterase 4D (PDE4D), vestigial like 2 (VGLL2), calcium channel voltage-dependent beta 2 subunit (CACNB2), and eyes absent homolog 4 (EYA4). In preferred embodiments, CSCs comprise a transgene encoding an inhibitory RNA molecule targeted to Sox5, Sox6, or Rod1 polynucleotide sequences.

In another embodiment of the invention, the modified CSCs contain a transgene that encodes a protein that promotes commitment to the myocyte lineage. Such proteins may include, but are not limited to, Nkx2.5, MEF2C, Notch1 receptor, and the intracellular domain of the Notch 1 receptor (N1ICD). It has recently been shown that activation of the Notch1 receptor on CSCs by the Jagged ligand expressed on neighboring cardiomyocytes in the mouse heart upregulates expression of Nkx2.5 and promotes the commitment of CSCs to the myocyte lineage. Furthermore, disruption of the Notch1 signaling cascade impairs myocardial regeneration after myocardial infarction. Thus, other suitable proteins that may be encoded by the transgene contained within modified CSCs may be proteins that enhance the Notch 1 signaling cascade.

The transgene may be introduced into the CSCs in various ways. Polynucleotide sequences comprising a miR sequence, an inhibitory RNA sequence, or a coding sequence may be directly transfected into isolated CSCs using standard methods in the art. Such methods include, but are not limited to, lipofection, DEAE-dextran-mediated transfection, microinjection, protoplast fusion, calcium phosphate precipitation, electroporation, and biolistic transformation. Alternatively, the transgene may be expressed in CSCs from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, a vector for expressing the transgene comprises a promoter "operably linked" to the transgene. The phrase "operably linked" or "under transcriptional control" as used herein means that the promoter is in the correct location and orientation in relation to a polynucleotide to control the initiation of transcription by RNA polymerase and expression of the polynucleotide. Several promoters are suitable for use in the vectors for expressing the transgene, including, but not limited to, RNA pol I promoter, RNA pol II promoter, RNA pol III promoter, and cytomegalovirus (CMV) promoter. Other useful promoters are discernible to one of ordinary skill in the art. In some embodiments, the promoter is an inducible promoter that allows one to control when the transgene is expressed. Suitable examples of inducible promoters include tetracycline-regulated promoters (tet on or tet off) and steroid-regulated promoters derived from glucocorticoid or estrogen receptors. Additionally, several inducible expression systems, such as the Rheoswitch® from New England Biolabs, are commercially available and may be used to express the transgene in isolated CSCs. Alternatively, the promoter operably linked to the transgene may be a promoter that is activated in specific cell types and/or at particular points in development. For example, the promoter may be derived from genes expressed early in myocyte differentiation, such as Nkx2.5, Mef2C, Tbx5 and myocardin.

In one embodiment of the invention, the modified CSCs comprise a transgene encoding a miR, wherein said transgene is expressed from a vector comprising a promoter operably linked to said transgene. Preferably, the miR encoded by the transgene is overexpressed in the CSCs. In another embodiment, the promoter is an inducible promoter. In another embodiment, the vector is a lentiviral vector. In a preferred embodiment, the transgene encodes miR-499.

In another embodiment of the invention, the modified CSCs comprise a transgene encoding an inhibitory RNA molecule, wherein said transgene is expressed from a vector comprising a promoter operably linked to said transgene. If the inhibitory RNA molecule is a siRNA molecule, the vector may comprise two convergent promoters such that the sense strand and the antisense strand are transcribed from the same nucleic acid sequence. In preferred embodiments, the expressed inhibitory RNA molecules target polynucleotide sequences encoding Sox5, Sox6, or Rod1 proteins.

The present invention also provides methods of regenerating damaged myocardium in a subject in need thereof. In one embodiment, the method comprises administering a pharmaceutical composition to an area of damaged myocardium in the subject, said pharmaceutical composition comprising modified cardiac stem cells as described herein, wherein said modified cardiac stem cells differentiate into mature, functional cardiomyocytes following administration, thereby regenerating the damaged myocardium. "Mature cardiomyocytes" refer to cardiomyocytes that exhibit the electrical, mechanical, and morphological characteristics of cardiomyocytes found in the adult heart. For example, mature cardiomyocytes do not possess the T-type calcium current, are generally larger than immature cardiomyocytes, are binucleate or multinucleate, have action potentials of shorter duration, and exhibit an increase in voltage-gated potassium currents. "Functional cardiomyocytes" are cardiomyocytes that are coupled to the viable existing myocardium (e.g. through gap and adherens junctions) and contribute to the normal function of the adult heart. In another embodiment, the regenerated myocardium exhibits the functional characteristics of adult myocardium. "Functional characteristics of adult myocardium" refer to electrical, mechanical, and morphological properties found exclusively in adult myocardium as opposed to fetal-neonatal myocardium. Such characteristics would include the presence of particular ion currents, the nature of muscle contraction, and the ability of the cardiomyocytes to divide (e.g. terminally differentiated) among others. For example, adult myocardium generates more tension than fetal-neonatal myocardium and possesses different calcium dynamics. Other morphological, mechanical, and electrical differences between adult myocardium and fetal-neonatal myocardium are known to those skilled in the art. See, for example, Baum and Palmisano (1997) Anesthesiology, Vol. 87: 1529-1548, which is herein incorporated by reference in its entirety. In preferred embodiments, the cardiac stem cells are autologous, that is, the cardiac stem cells are obtained from the same patient receiving the pharmaceutical composition. In another embodiment, the subject requiring repair of damaged myocardium is suffering from a myocardial infarction.

In another embodiment of the invention, the method comprises extracting cardiac stem cells from the subject; incorporating a transgene into said extracted cardiac stem cells, wherein said transgene encodes a microRNA; and administering the cardiac stem cells comprising the transgene to an area of damaged myocardium in the subject, wherein the cardiac stem cells differentiate into mature, functional cardiomyocytes following administration, thereby regenerating the damaged myocardium. In a preferred embodiment, the transgene encodes miR-499. In another embodiment, the microRNA is overexpressed in the extracted cardiac stem cells. In yet another embodiment, extracting cardiac stem cells from the subject comprises harvesting myocardial tissue from the subject and isolating the cardiac stem cells from said myocardial tissue. In a particularly preferred embodiment, the subject is human.

In still another embodiment of the invention, the method further comprises administering vascular progenitor cells to an area of damaged myocardium in the subject, wherein the vascular progenitor cells are autologous. In another embodiment, the vascular progenitor cells differentiate into endothelial cells and smooth muscle cells, thereby generating new vascular structures. The vascular structures formed by the differentiation of the VPCs would complement the regeneration of myocardial tissue induced by the differentiation of the modified CSCs by providing the necessary vasculature to supply oxygen to the newly generated myocardial tissue. The VPCs may be administered simultaneously with the modified CSCs or at some particular time after administration of the modified CSCs.

The present invention also provides a method for regenerating damaged myocardium in a subject in need thereof by administering unmodified CSCs and a transgene encoding a microRNA. In preferred embodiments, the unmodified CSCs are autologous or isolated from the subject to which they will be administered. Unmodified CSCs can differentiate into myocytes, smooth muscle cells, and endothelial cells, which can assemble into new myocardium and vascular structures. As discussed above, the majority of newly formed myocytes produced by unmodified CSCs fail to attain the mature cardiomyocyte phenotype. Subsequent administration of a transgene encoding a microRNA to the newly formed myocytes promotes further differentiation and maturation such that the newly formed myocytes exhibit the adult phenotype. Thus, in one embodiment of the invention, the method comprises administering cardiac stem cells to an area of damaged myocardium in a subject in need thereof, wherein the cardiac stem cells differentiate into myocytes, smooth muscle cells, and endothelial cells after their administration, thereby regenerating the damaged myocardium; and administering a transgene encoding a microRNA to the area of regenerated myocardium, wherein the regenerated myocardium exhibits the functional characteristics of adult myocardium following transgene administration. In a preferred embodiment of the invention, the microRNA is miR-499.

The transgene encoding the microRNA can be administered to the newly regenerated myocardium by various methods known to those skilled in the art for delivering nucleic acids, including, but not limited to, macromolecule complexes, nanocapsules, microspheres, beads, and lipid-based systems including oil-in-water emulsions, micelles, mixed micelles, and liposomes. The transgene may be provided as a polynucleotide comprising the microRNA sequence or may be expressed from a vector, such as a viral vector as described above. In preferred embodiments, the transgene encoding the microRNA is expressed from a lentiviral vector.

Thus, the invention involves administering a therapeutically effective dose or amount of stem cells to the heart. An effective dose is an amount sufficient to effect a beneficial or desired clinical result. Said dose could be administered in one or more administrations. As illustrated in the examples in co-pending U.S. Application Publication No. 2006/0239983, filed Feb. 16, 2006, which is herein incorporated by reference, $2 \times 10^4$-$1 \times 10^5$ stem cells were sufficient to effect myocardial repair and regeneration in a mouse model of myocardial infarction. While there would be an obvious size difference between the hearts of a mouse and a human, it is possible that this range of stem cells would be sufficient in a human as well. However, the precise determination of what would be considered an effective dose may be based on factors individual to each patient, including their size, age, area of myocardial damage, and amount of time since damage. One skilled in the art, specifically a physician or cardiologist, would be able to determine the number of stem cells that would constitute an effective dose without undue experimentation.

In some embodiments of the invention, the modified cardiac stem cells are activated prior to administration to a patient. Activation of the stem cells may be accomplished by exposing the stem cells to one or more cytokines, such as hepatocyte growth factor (HGF) or insulin-like growth factor-1 (IGF-1). HGF positively influences stem cell migration and homing through the activation of the c-Met receptor (Kollet et al. (2003) J. Clin. Invest. 112: 160-169; Linke et al. (2005) Proc. Natl. Acad. Sci. USA 102: 8966-8971; Rosu-Myles et al. (2005) J. Cell. Sci. 118: 4343-4352; Urbanek et al. (2005) Circ. Res. 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) Diabetes 50: 1414-1424; Torella et al. (2004) Circ. Res. 94: 514-524; Davis et al. (2006) Proc. Natl. Acad. Sci. USA 103: 8155-8160). In a preferred embodiment, the modified cardiac stem cells are contacted with HGF and/or IGF-1. In one embodiment, HGF is present in an amount of about 0.1-400 ng/ml. In another embodiment, HGF is present in an amount of about 25, about 50, about 75, about 100, about 125, about 150, about 175, about 200, about 225, about 250, about 275, about 300, about 325, about 350, about 375 or about 400 ng/ml. In another embodiment, IGF-1 is present in an amount of about 0.1-500 ng/ml. In yet a further embodiment, IGF-1 is present in an amount of about 25, about 50, about 75, about 100, about 125, about 150, about 175, about 200, about 225, about 250, about 275, about 300, about 325, about 350, about 375, about 400, about 425, about 450, about 475, or about 500 ng/ml.

Some other non-limiting examples of cytokines that are suitable for the activation of the modified cardiac stem cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-β2, Transforming Growth Factor-□β3, Vascular Endothelial Growth Factor, Wnt1, Wnt3a, and Wnt5a, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol Chem. 280: 41342-41351; Barnabe-Heider et al. (2005) Neuron 48:253-265; Madlambayan et al. (2005) Exp Hematol 33:1229-1239; Kamanga-Sollo et al. (2005) Exp Cell Res 311:167-176; Heese et al. (2005) Neuro-oncol. 7:476-484; He et al. (2005) Am J. Physiol. 289:H968-H972; Beattie et al. (2005) Stein Cells 23:489-495; Sekiya et al. (2005) Cell Tissue Res 320: 269-276; Weidt (2004) Stem Cells 22:890-896; Encabo et al (2004) Stem Cells 22:725-740; and Buytaeri-Hoefen et al. (2004) Stem Cells 22:669-674, the entire text of each of which is incorporated herein by reference.

Functional variants of the above-mentioned cytokines can also be employed in the invention. Functional cytokine variants would retain the ability to bind and activate their corresponding receptors. Variants can include amino acid substitutions, insertions, deletions, alternative splice variants, or fragments of the native protein. For example, NK1 and NK2 are natural splice variants of HGF, which are able to bind to the c-MET receptor. These types of naturally occurring splice variants as well engineered variants of the cytokine proteins that retain function are contemplated by the invention.

The modified cardiac stem cells as well as other adult stem cells, such as VPCs, may be administered to the heart by injection. The injection is preferably intramyocardial. As one skilled in the art would be aware, this is the preferred method of delivery for stem cells as the heart is a functioning muscle. Injection by this route ensures that the injected material will not be lost due to the contracting movements of the heart. In one embodiment, the stem cells are administered to the border zone of the damaged myocardium. Damaged myocardium, which typically contains infarcted tissue, is visible grossly allowing for this specific placement of the stem cells.

In a further aspect of the invention, the stem cells are administered by injection transendocardially or trans-epicardially. In a preferred embodiment, a catheter-based approach to deliver the trans-endocardial injection of stem cells is employed. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) Basic Appl. Myol. 13: 11-14; Patel et al. (2005) The Journal of Thoracic and Cardiovascular Surgery 130:1631-38; and Perrin et al. (2003) Circulation 107: 2294-2302; the text of each of which are incorporated herein in their entirety. One of skill in the art will recognize other useful methods of delivery or implantation which can be utilized with the present invention, including those described in Dawn et al. (2005) Proc. Natl. Acad. Sci. USA 102, 3766-3771, the contents of which are incorporated herein in their entirety.

The compositions and methods of the present invention are useful for the treatment of cardiovascular disease, including, but not limited to, atherosclerosis, ischemia, myocardial infarction, hypertension, restenosis, angina pectoris, rheumatic heart disease, congenital cardiovascular defects, age-related cardiomyopathy, and arterial inflammation and other disease of the arteries, arterioles and capillaries. Specifically, the methods of the present invention provide for the repair and/or regeneration of damaged myocardium resulting from one of the diseases listed above or from the general decline of myocardial cells with age.

The present invention contemplates pharmaceutical compositions comprising an effective amount of modified stem cells described herein and a pharmaceutically acceptable carrier. In preferred embodiments, the pharmaceutical compositions comprise cardiac stem cells, said cardiac stem cells comprising a transgene. When administering a composition of the present invention, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils. Examples of compositions comprising modified stem cells of the invention include liquid preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Pharmaceutical compositions of the invention, are conveniently provided as liquid preparations, e.g., isotonic aqueous solutions, suspensions, emulsions or viscous compositions which may be buffered to a selected pH. Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

Sterile injectable solutions can be prepared by incorporating the compounds utilized in practicing the present invention in the required amount of the appropriate solvent with various amounts of the other ingredients, as desired.

The quantity of the pharmaceutical composition to be administered will vary for the patient being treated. In a preferred embodiment, $2 \times 10^4$-$1 \times 10^5$ modified cardiac stem cells are administered to the patient. However, the precise determination of what would be considered an effective dose may be based on factors individual to each patient, including their size, age, area of damaged myocardium, and amount of time since damage. Thus, the skilled artisan can readily determine the dosages and the amount of compound and optional additives, vehicles, and/or carrier in compositions to be administered in methods of the invention. Typically, any additives (in addition to the active modified stem cells) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation. In some embodiments, the pharmaceutical composition further comprises VPCs. $1\times10^4$-$1\times10^5$ VPCs may be administered to the patient. However, the precise dosage will depend on the type of cardiac disease to be treated, the amount of myocardial and coronary vasculature damage, characteristics of the individual patient, and the dosage of modified cardiac stem cells the patient has received or is going to receive. Adjustments of VPC dosage can be readily ascertained by the skilled artisan.

The inventive compositions of this invention are prepared by mixing the ingredients following generally accepted procedures. The mixture may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat heart failure and cardiovascular diseases, including, but not limited to, atherosclerosis, ischemia, hypertension, myocardial infarction, restenosis, angina pectoris, rheumatic heart disease, congenital cardiovascular defects and arterial inflammation and other diseases of the arteries, arterioles and capillaries or related complaint. Accordingly, the invention involves the administration of modified adult stem cells as herein discussed for the treatment or prevention of any one or more of these conditions or other conditions involving weakness in the heart. And, advantageous routes of administration involves those best suited for treating these conditions, such as via injection, including, but are not limited to intravenous, intraarterial, intramuscular, intramyocardial, transendocardial, and trans-epicardial.

This invention is further illustrated by the following additional examples that should not be construed as limiting. The contents of all references, patents and published patent applications cited throughout this application, as well as the Figures, are incorporated herein by reference in their entirety.

EXAMPLES

Example 1

Specific microRNAs are Differentially Expressed in Adult Cardiomyocytes and Cardiac Stem Cells Studies in embryonic stem cells, neural stem cells and hematopoietic stem cells have shown that the regulation of self-renewal, multipotentiality and commitment occurs only in part at the transcriptional level (Ramalho-Santos et al., 2002; Ivanova et al., 2002; Bruno et al., 2004; and Bhattacharya et al., 2004). Although transcription factors are critical modulators of stem cell growth and differentiation, post-transcriptional gene regulation is emerging as an unexpected mechanism of progenitor cell fate. MicroRNAs (miRs) are small RNAs that regulate the post-transcriptional expression of proteins generated from mRNA transcripts (Alvarez-Garcia and Miska, 2005; Chapman and Carrington, 2007; and Chu and Rana, 2007). They are transcribed by RNA polymerase II and subsequently processed by the RNase III enzymes, Drosha and Dicer, into mature miRs of ~20-22 nucleotides (Tijsterman and Plasterk, 2004; and Gregory et al, 2006). These RNA strands bind to proteins of the Argonaute family forming RNA-induced silencing complexes that mediate distinct gene silencing mechanisms (Peters and Meister, 2007). MiRs inhibit gene expression by modulating the stability and/or the translation of the target mRNA (Alvarez-Garcia and Miska, 2005; Chapman and Carrington, 2007; and Chu and Rana, 2007). The degree of sequence complementarity with the target determines whether the miR inhibits protein translation by binding to the 3' untranslated region (3'-UTR) (less complementary) or degrades the mRNA (100% complementary). Additionally, miRs promote gene silencing through chromatin remodeling. Enzymes that modify histones and DNA methyltransferases are miR-targets (Tuddenham et al., 2006; Saetrom et al., 2007; and Chuang and Jones, 2007). In turn, DNA methylation and histone post-translational modifications regulate the quantity of several miRs (Saetrom et al., 2007; Chuang and Jones, 2007; and Yu et al., 2005).

Different sets of miRs are expected to be present in multipotent cardiac stem cells (CSCs) and their progeny. Importantly, miRs may repress stem cell maintenance genes promoting the differentiation of CSCs into cardiomyocytes. The transition from the primitive to the committed state of CSCs requires a rapid switch in gene expression. Although the pool of transcription factors may be replaced, the residual transcripts of the stemness-related genes that were highly expressed in the previous undifferentiated stage have to be silenced; and miRs can simultaneously repress multiple targets (Alvarez-Garcia and Miska, 2005; Chapman and Carrington, 2007; and Chu and Rana, 2007). Thus, it is possible that miRs that are highly expressed in cardiomyocytes and minimally present or absent in undifferentiated CPCs may be involved in the maintenance of the terminally differentiated state of myocytes and may translocate to neighboring CPCs initiating their differentiation.

In this Example, a group of miRs that are particularly abundant in myocytes were identified by employing a miR array approach. As shown in FIG. 1, several miRs, including miR-1, miR-499, miR-133, miR-30, miR-26 and let-7, were found to be expressed in rat cardiomyocytes. However, only the expression of miR-1, miR-499 and miR-133 differed significantly in myocytes and CSCs. Both miR-1 and miR-133 have been shown to be involved in the modulation of cardiac growth. The function of miR-1 appears to be mostly related to cardiac development since its overexpression inhibits myocyte proliferation and the expansion of the ventricular myocardium in the embryonic heart (Zhao et al., 2005). Additionally, targeted deletion of miR-1-2 carries a 50% lethality predominantly mediated by ventricular-septal defects (Zhao et al., 2007). Importantly, in the adult heart, miR-1 is down-regulated during the development of the myocyte hypertrophic response following aortic banding (Sayed et al., 2007) and direct injection of miR-1 in the infarcted myocardium results in severe rhythm disturbances (Yang et al., 2007). Similarly, miR-133 is downregulated during myocardial hypertrophy in animals and humans (Care et al., 2007). This inhibitory function of miR-133 in myocyte hypertrophy has been confirmed in vitro with neonatal and adult mouse myocytes (Sayed et al., 2007). Thus, since both miR-1 and miR-133 prevent myocyte hypertrophy (Sayed et al., 2007; Tatsuguchi et al., 2007; van Rooij and Olson, 2007), it is unlikely that their function is linked to CSC differentiation and formation of adult myocytes.

Figure 2:
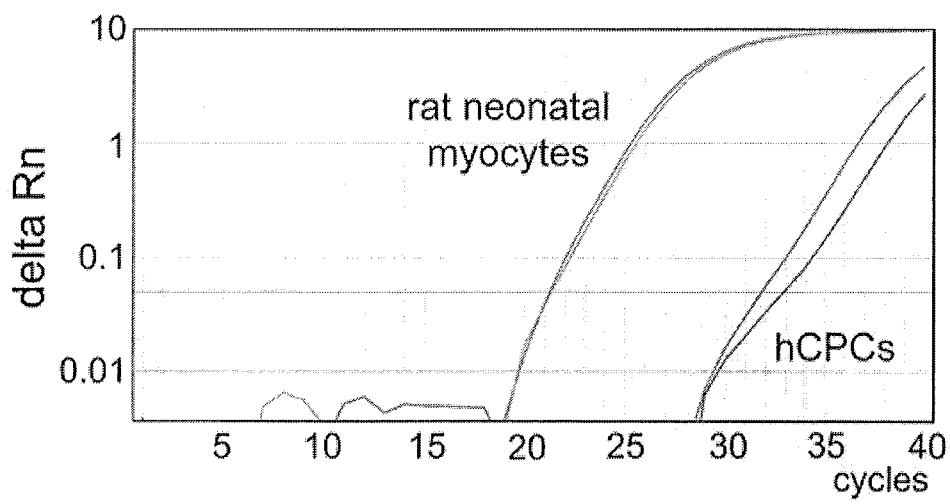
FIG. 2. A. Quantitative RT-PCR for miR-499. Neonatal myocytes have a significantly higher level of expression of miR-499 than human cardiac stem cells (hCSCs). B. The Myh7b gene has a low degree of homology with β-MHC and contains Nkx2.5 consensus sites in its putative promoter region.

MiR-499 is highly expressed in the rat heart and its quantity is ~500-fold higher in myocytes than in CSCs (FIGS. 1 and 2A). MiR-499 has been discovered recently (Berezikov et al., 2005; and Bentwich et al., 2005). Nearly one-third of miRs is encoded within the introns of primary genes and is processed out of the primary gene pre-mRNA rather than being transcribed as separate transcripts (Baskerville and Bartel, 2005). Therefore, the expression of these miRs is under the control of the promoter driving the transcription of the primary mRNA (Baskerville and Bartel, 2005). MiR-499 is encoded within the intron of the newly identified Myh7b gene, which encodes a member of the sarcomeric myosin heavy chain (MHC) protein family (Nagase et al., 2000; and Desjardins et al., 2002). The Myh7b gene is expressed in the brain, heart, skeletal muscle and testis (Nagase et al., 2000) and has a 70% degree of homology with β-MHC both at the mRNA and protein levels (FIG. 2B). This degree of homology is lower than the similarity between α- and β-MHC indicating that Myh7b is a distinct gene. Additionally, the putative promoter region of Myh7b contains Nkx2.5 binding consensus sequences (FIG. 2B). Importantly, miR-499 and Myh7b are encoded in the same orientation in all species including humans indicating that the RNAs of these two sequences are simultaneously transcribed.

Example 2

MiR-499 Targets Rod1 and Sox D Proteins

Figure 3:
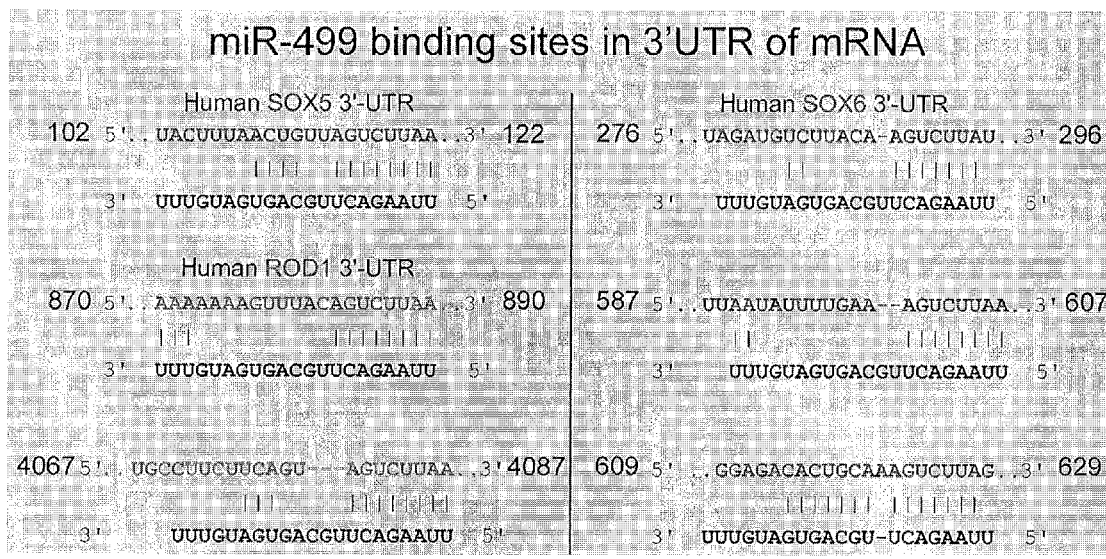
FIG. 3. One, two and three miR-499 binding sites are present in the 3'-UTR of human Sox5 (red (SEQ ID NO.: 51)), Rod 1 (blue (SEQ ID NOs.: 52 and 53)) and Sox6 (green (SEQ ID NOs.: 54-56)) mRNA, respectively. Black sequences correspond to mature miR-499 (SEQ ID NO.: 5).

By employing the web-based target-prediction program TargetScan version 4, ~200 putative target genes of miR-499 were identified. Among the genes that scored as strong predicted-targets, based on high complementarity and evolutionary conservation, 3 genes were selected for further study for their potential role in CSC division and differentiation: SRY (sex determining region Y)-box 5 (Sox5) and 6 (Sox6) and Regulator of Differentiation 1 (Rod1). The 3'-UTR of Sox5, Sox6 and Rod1 gene contains 1, 3 and 2 evolutionary conserved miR-499 binding sites, respectively. These putative miR-499 binding sites in the 3'-UTR of Sox5, Sox6 and Rod1 mRNA showed high complementarity with the seed region of miR-499 (FIG. 3).

SRY-related high-mobility-group box (Sox) transcription factors are implicated in cell fate determination in multiple organs (Lefebvre et al., 2007). They are encoded by twenty genes in humans and mice and share a highly conserved high-mobility-group box domain that was originally identified in SRY, the sex-determining gene on the Y chromosome (Sinclair et al., 1990; and Gubbay et al., 1990). Based on the similarity in protein sequence, Sox transcription factors have been divided in 8 groups, A to H (Lefebvre et al., 2007). Although the function of Sox genes remains largely unknown, SoxB1 genes appear to control the preservation of sternness in primitive cells (Graham et al., 2003; Bylund et al., 2003; Pevny and Placzek, 2005; and Wegner and Stolt, 2005), while Sry (SoxA), SoxC, SoxE and SoxF genes promote the specification of lineage fate in stem cells and their early stages of differentiation (Pennisi et al., 2000; Maka et al., 2005; Wilson et al., 2005; Dewing et al., 2006; Matsui et al., 2006; O'Donnell et al., 2006; and Bergsland et al., 2006). SoxD genes, which include Sox5 and Sox6, modulate terminal maturation of committed progenitor cells acting downstream with respect to the developmental decision of cell fate (Smits et al., 2001; Yi et al., 2006; Dumitriu et al., 2006; and Stolt et al., 2006). Deletion of the Sox6 gene in mice is associated with alterations in cardiac conduction (Hagiwara et al., 2000). In vitro data collected in the embryonic carcinoma cell line P19CL6 suggest that the expression of Sox6 is coupled with commitment to the myocyte lineage but, surprisingly, with a downregulation of the α1c subunit of the L-type Ca2+ channels (Cohen-Barak et al., 2003). Rod1 is the mammalian homologue of nrd1 which is an RNA binding protein that acts as negative regulator of differentiation in fission yeasts (Tsukahara et al., 1998). Rod1 was isolated in 1999 and found to be able to block differentiation of erythrocytes and megakaryocytes (Yamamoto et al., 1999).

Reporter assays were performed to validate the putative miR-499-target gene combination. This strategy allowed the determination of whether miR-499 binds to the transcripts of Sox6 and Rod1 genes and interferes with their translation. The 3'-UTR sequences of the two genes were obtained by PCR, sequenced and ligated at a position downstream of the luciferase coding sequence in reporter plasmids (see method section below). In this system, the potential interaction between miR-499 and the 3'-UTR of Sox6 and Rod1 should result in downregulation of luciferase expression. A β-gal-expressing plasmid was employed to normalize luciferase activity. The reporter construct was under the control of the cytomegalovirus (CMV) promoter. Mouse NIH-3T3 fibroblasts were transfected with pre-miR-499. This cell line was selected to minimize the influence of endogenous expression of miR-499. One day later, cells were co-transfected with luciferase reporter plasmids (Sox6 or Rod1) and β-gal expression vectors. Then, cells were harvested 24 hours later. A pre-miR random sequence was used as negative control, and basal expression level of luciferase was measured in the absence of miR-499. The decrease in luciferase activity documented that the presence of miR-499 markedly interfered with the translation of the two constructs indicating that Sox6 and Rod1 are target genes of miR-499 (FIG. 4A).

Additional reporter assays were performed utilizing a plasmid carrying miR-499. A murine genomic DNA fragment of 254 bp including miR-499 was cloned into a plasmid downstream of the CMV promoter. The plasmid (CMV-miR-499) was transfected into NIH-3T3 fibroblasts. Nearly 105 cells were seeded and transfected with 1 µg of CMV-miR-499. Cells were harvested 3 days later for RNA isolation. Cells transfected with blank plasmids (CMV-blank) were used as negative control. About 1 ng of total RNA from each condition was used to quantify the mature form of miR-499; small nucleolar RNA sno-412 was employed as endogenous control RNA for normalization of miR-499 expression. As expected, 3T3 cells transfected with CMV-blank showed minimal expression level of miR-499 whereas cells containing CMV-miR-499 had ~5,500-fold higher level of expression (FIG. 4B, C). To document that the transcribed miR-499 in the cells was functional, luciferase assay was performed as discussed above. 3T3 cells were co-transfected with CMV-miR-499 and reporter plasmids containing the luciferase coding sequence alone or conjugated with the 3'-UTR of Sox6 and Rod1. CMV-blank was used as negative control and to adjust the total amount of DNA to be transfected. Importantly, cells transfected with luciferase reporter lacking 3'-UTR showed intact levels of luciferase activity. Conversely, a striking decrease in luciferase activity was measured in cells that received reporter plasmids with 3'-UTR of Sox6 and Rod1. The downregulation of luciferase activity occurred in a dose-dependent manner when increasing concentrations of CMV-miR-499 plasmids were used (FIG. 4D).

Figure 4:
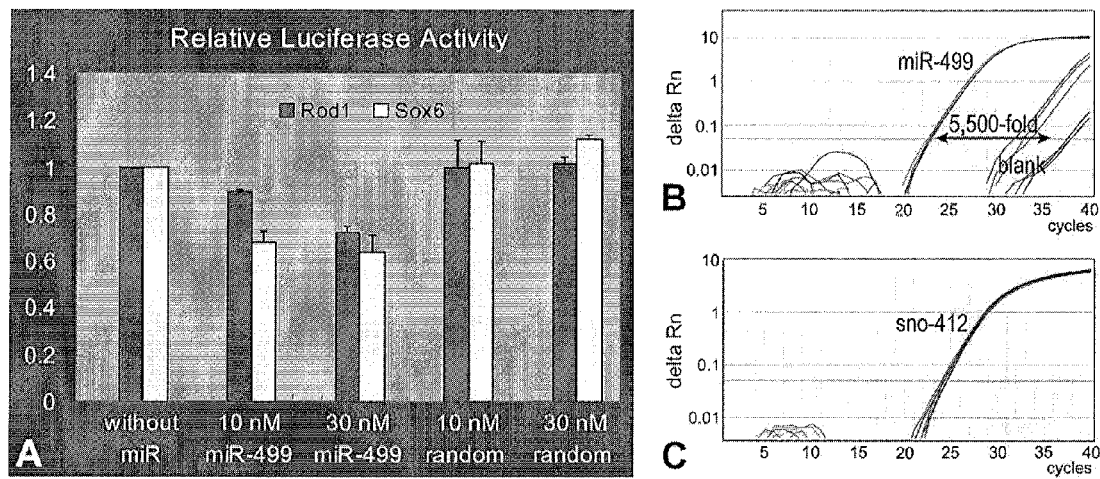
FIG. 4. A. 3T3 cells were co-transfected with pre-miR-499 and reporter plasmids in which the luciferase coding sequence was placed under the control of the CMV promoter. The 3'-UTR of Rod1 and Sox6 genes were cloned downstream of luciferase. The presence of miR-499 induced a decrease in luciferase activity in the transfected cells. B, C. Quantitative RT-PCR for the expression of miR-499 in 3T3 transfected with an expression plasmid carrying miR-499. With respect to 3T3 cells transfected with blank plasmids, the quantity of miR-499 increased 5,500-fold. Small nucleolar RNA (sno-412) was employed for normalization. These cells were employed for the reporter assay in panel D. D. miR-499 overexpressing 3T3 cells were transfected with reporter plasmids in which the 3'-UTR of Rod1 and Sox6 genes were cloned downstream of luciferase. Increasing amounts of miR-499 expression plasmid were used for transfection (0-0.8 μg). The decrease in luciferase activity paralleled the increase in miR-499 expression. Luciferase only denotes 3T3 cells transfected with a reporter plasmid without 3'-UTR of Rod1 and Sox6 genes.
Figure 4:
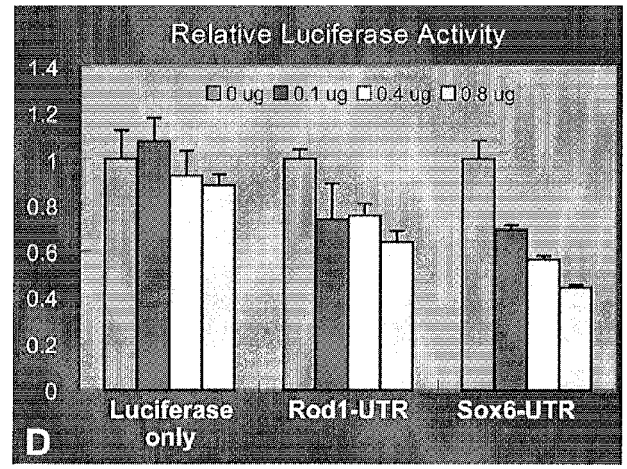

The data in FIG. 4 indicate that Sox6 and Rod1 represent actual target genes of miR-499, demonstrating a functional role for miR-499, which may have important implications in cardiac homeostasis and regeneration. CSCs have recently been identified and characterized in the human heart and have been found to regenerate large quantities of immature myocytes (Bearzi et al., 2007). MiR-499 may be able to favor the differentiation of newly formed human myocytes and promote their acquisition of the adult phenotype.

Importantly, the self-renewal, clonogenicity and multipotentiality of human cardiac stem cells (hCSCs) were documented in vivo by genetic tagging (Hosoda et al., 2008). Integration site analysis with a PCR-based method that can distinguish the progeny of each transduced stem cell by its unique proviral-genomic fusion sequence was performed. hCSCs were infected with EGFP-lentivirus and employed to induce cardiac repair after infarction. hCSCs, myocytes, endothelial cells and fibroblasts were collected from the regenerated myocardium and the insertion-site of the EGFP-gene in the human genome was detected by nested PCR. This novel approach revealed that hCSCs acquire a cardiac phenotype in vivo and myocardial regeneration has a polyclonal origin (Hosoda et al., 2008). Thus, the commitment of hCSCs to myocytes and their terminal maturation may be associated with (a) translocation of miR-499 from cardiomyocytes to neighboring hCSCs through gap junctions; (b) accumulation of miR-499 in hCSCs; (c) stable or decreased levels of the transcripts of the target genes of miR-499, Sox5, Sox6 and Rod1; (d) decrease in Sox5, Sox6 and Rod1 proteins; (e) upregulation of myocyte-specific transcription factors and contractile proteins; and (f) acquisition of electrical, mechanical and Ca2+ transient properties of functionally-competent adult myocytes.

Figure 5:
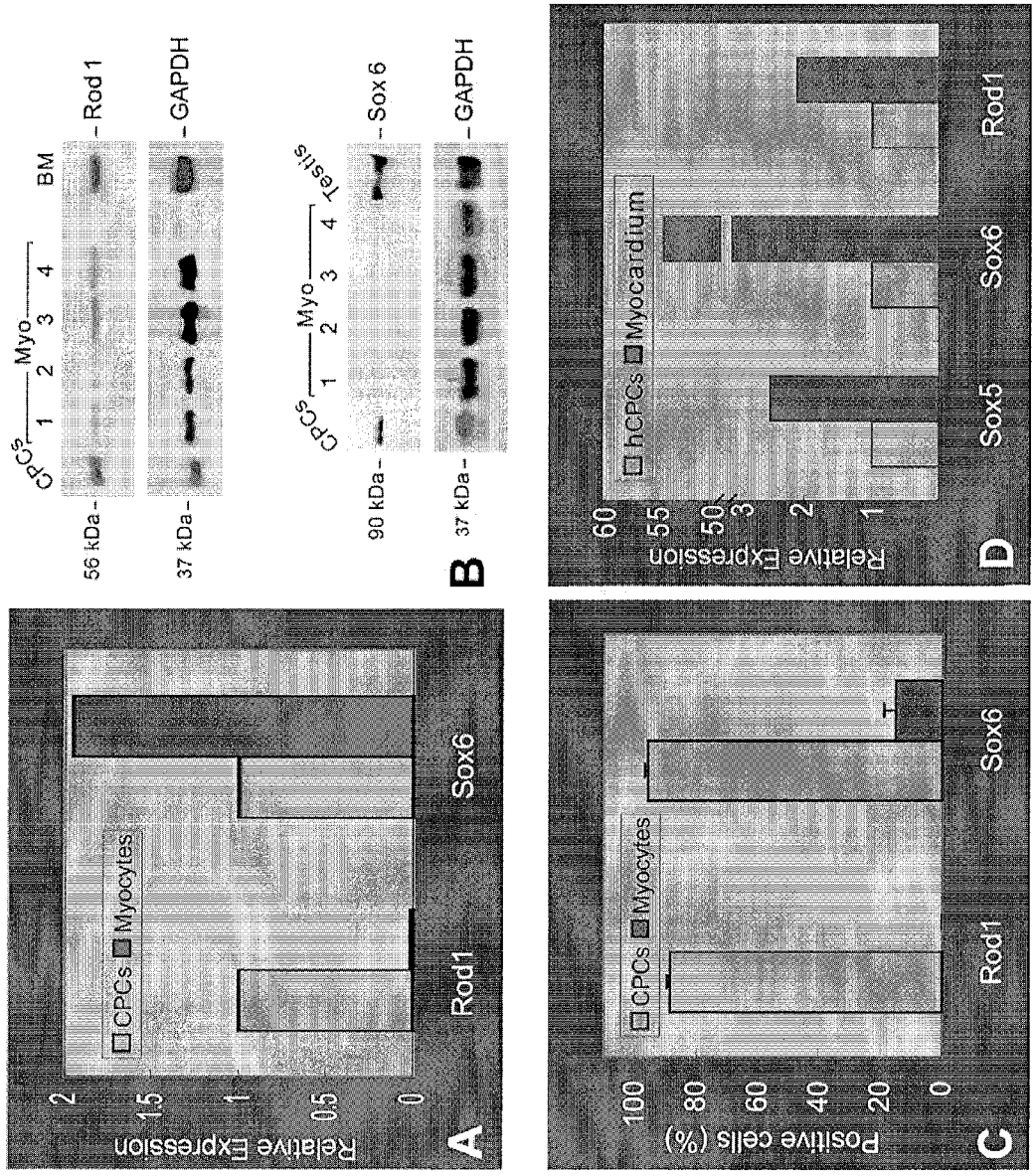
FIG. 5. A. Quantitative RT-PCR for Rod1 and Sox6 transcripts in CSCs and myocytes obtained from the rat heart. B. Western blotting for Rod1 and Sox6 proteins in rat CSCs and myocytes. GAPDH was used for normalization. C. The expression of Rod1 and Sox6 was measured quantitatively by immunocytochemistry in rat CSCs and myocytes. The fraction of cells positive for the two proteins is shown. D. Quantitative RT-PCR for Sox5, Sox6 and Rod1 transcripts in hCSCs and human myocardium.

The following experiments were performed to test whether miR-499 is a crucial modulator of the differentiation of CSCs into cardiomyocytes and whether this function of miR-499 is mediated by the repression of Sox6 and Rod1. First, the transcript levels of Sox6 and Rod1 were measured in rat myocytes, human myocardium, rat CSCs and hCSCs by quantitative RT-PCR. Sox6 mRNA was 2-fold higher and Rod1 mRNA was 98% lower in rat myocytes than in rat CSCs (FIG. 5A). The transcripts of the three genes, Sox5, Sox6 and Rod1 were highly expressed in the human myocardium (FIG. 5D). By Western blotting, the protein levels of Sox6 and Rod1 were significantly decreased in rat myocytes with respect to CSCs suggesting that miR-499 promotes degradation and/or inhibition of translation of these target genes (FIG. 5B). Importantly, the decrease in expression of Sox6 and Rod1 protein in rat myocytes (FIG. 5B,C) is consistent with the higher quantity of miR-499 in these cells. These findings support the role of miR-499 and its target genes Sox6 and Rod1 in the differentiation of CSCs into cardiomyocytes.

Specific Methods

Human CSCs.

Discarded myocardial samples (n=10) were obtained from patients who underwent open heart surgery. hCSCs were harvested by enzymatic dissociation as previously described (Bearzi et al., 2007). Briefly, cardiac tissue samples were incubated in a solution containing collagenase to obtain a single cell suspension. Cells were labeled with a c-kit antibody conjugated with magnetic beads (Miltenyi). hCSCs were then expanded, infected with a lentivirus carrying EGFP and employed for further studies. Expanded hCSCs were stained with a c-kit antibody and sorted by FACS prior to their use to collect a highly homogenous population of undifferentiated cells with a 95-98% degree of enrichment for the stem cell antigen c-kit. This step also allows the assessment of the efficiency of EGFP infection.

Construction of Plasmids.

Expression plasmids encoding miR-499, Sox5, Sox6, and Rod1 as well as luciferase reporter plasmids were prepared as follows.

a) miR-499 Expression Plasmid.

The pMIR-REPORT β-gal Control Plasmid was modified by digesting with BamH1 and Hind3, blunted with T4 DNA polymerase, and then self-ligated with T4 DNA ligase to serve as blank plasmid (CMV-blank). Mouse genomic DNA coding the stem loop of miR-499 together with the two flanking regions of ~100 bp each was amplified with the primers indicated below. The construct was ligated to replace the β-gal gene in the Control Plasmid and obtain the miR-499 expression plasmid (CMV-miR-499).

```
miR-499-BamH1-F:
                                   (SEQ ID NO.: 12)
5'-CCT AAG GAT CCC ACG CCC CCT ACA GGC TGC CAC-3' miR-499-Hind3-R:
                                   (SEQ ID NO.: 13)
5'-ACC TAA AGC TTC ACC GCC CCC CCA CCC CCA G-3'
```

To confirm the function of the plasmids, 105 3T3 fibroblasts were transfected with 1 µg of CMV-blank or CMV-miR-499; 3 days later, RNA was extracted and miR-499 was measured by quantitative RT-PCR (see below).

b) Luciferase reporter plasmids. The pMIR-REPORT Luciferase and pMIR-REPORT β-gal Control Plasmid were obtained from Applied Biosystems and utilized for transfection with or without modifications. Mouse genomic DNA was amplified to obtain the 3' untranslated region (3'-UTR) of Sox6 (5.6 kb) and Rod1 (5.0 kb) genes using the primers indicated below. However, the sequence was partly modified (see underlined nucleotides) to introduce restriction sites in the amplicons.

```
mSox6-MluI-F2:
                                   (SEQ ID NO.: 14)
5'-TGT TTG ACG CGT TAA AAC ACT CTG ACA TTT CGC

TCC-3' mSox6-PmeI-R:
                                   (SEQ ID NO.: 15)
5'-AGT CCT GTT TAA ACT TCT CTT TAT CAC TAT CCA

GAG-3' mRod1-MluI-F:
                                   (SEQ ID NO.: 16)
5'-TGA CCT ACG CGT GAA ATT GTC TCC TTA TAC TGG

AC-3' mRod1-PmeI-R:
                                   (SEQ ID NO.: 17)
5'-AAA AGG GTT TAA ACA ATG CTA TAT GTG TTA GGA

AAA GAG GC-3'
```

The reaction mixture consisted of 22.5 µl of AccuPrime Pfx SuperMix (Invitrogen), 5 pmole each of Forward and Reverse primers and 50 ng of genomic DNA extracted from adult mouse heart using QIAamp DNA Mini Kit (Qiagen). PCR cycling conditions were as follows: 95° C. for 5 min followed by 35 cycles of amplification (95° C. for 15 sec, 60° C. for 30 sec and 68° C. for 5 min 30 sec) and the last step at 68° C. for 5 min. PCR products were run on 0.6% agarose/1×TBE gel. The DNA bands were cut out and DNA was extracted using QIAEX II Gel Extraction Kit (Qiagen). Following restriction digestion with Mlul and PmeI for Sox6 3'-UTR and Rod1 3'-UTR, DNA sequences were directionally ligated to pMIR-REPORT Luciferase plasmid (Applied Biosystems). This plasmid has a multiple cloning site downstream of the luciferase gene which is placed under the control of the CMV promoter. To exclude the possibility of erroneous amplification events, constructs were fully sequenced utilizing the pMIR-REPORT-1 primer (5'-AGG CGA TTA AGT TGG GTA-3' (SEQ ID NO.: 18)) which is located downstream of the multiple cloning site. Additional primers were designed at a distance of 500 bp with each other within the amplicons and employed to verify construct sequences.

A similar approach is employed to obtain a reporter plasmid in which luciferase is placed upstream from the 3'-UTR of Sox5. To obtain the 3'-UTR of Sox5, the following primers are used:

mSox5-NaeI-F:
(SEQ ID NO.: 19)
5'-ATA AGG GCC GGC AGA CTG TGG TGA GCC GAG GAC TT-3' mSox5-PmeI-R:
(SEQ ID NO.: 20)
5'-TTT CTT TTT AAA AAT TGT AGC ACA GAA CAA C-3' c) siRNA Transfection.

siRNA for human Sox5, Sox6 and Rod1 is obtained from Dharmacon and corresponds to a mixture of 4 different duplexes for each gene. siRNA has a highly complimentary sequence to induce the degradation of the target mRNA. For transfection, a final concentration of 100 nM siRNAs against Sox5, Sox6, Rod1 or random control siRNA is used together with TransPass R2 Transfection Reagent (New England Biolabs) to induce interference in hCSCs. Non-transfected cells will be used as control.

d) Expression Plasmids for Sox5, Sox6 and Rod1.

PCR is performed such that Hind3 and EcoR1 restriction sites are introduced in the amplicon at the 5'- and 3'-side, respectively. The amplicons containing the full coding sequence of each human gene is ligated into the multiple cloning site of pcDNA3 expression plasmid following restriction digestion with Hind3 and EcoR1.

hSox5-Hind3-F:
(SEQ ID NO.: 21)
5'-TTT AGA AGC TTT GGA CTC ACT TGA CAG G-3' hSox5-EcoR1-R:
(SEQ ID NO.: 22)
5'-GTT AGG AAT TCT TTA AGT CCT AAG GTC AC-3' hSox6-Hind3-F:
(SEQ ID NO.: 23)
5'-ATG GTA AGC TTC AAG GAC ATG AAA GGT T-3' hSox6-EcoR1-R:
(SEQ ID NO.: 24)
5'-TAC TTG AAT TCA GCA AAC AAA AAC TCC TC-3' hRod1-Hind3-F:
(SEQ ID NO.: 25)
5'-AGC CAA AGC TTG CTT GTC CCC GGA ACC G-3' hRod1-EcoR1-R:
(SEQ ID NO.: 26)
5'-GAG AAG AAT TCA CAG AAA AGT CAG ATT GTA G-3'

Quantitative RT-PCR for miR-499.

RNA was extracted from hCSCs, rat neonatal myocytes, C2C12 myoblasts and 3T3 cells with mirVana miRNA isolation kit (Applied Biosystems). One ng of total RNA including the small RNA fraction was reverse transcribed utilizing a specific primer for miR-499 and the TaqMan MicroRNA reverse transcription kit (Applied Biosystems). The cDNA was subsequently amplified with forward and reverse primers together with FAM-labeled probe for the quantification. Equal amounts of RNA were used for the quantification of small nucleolar RNA RNU44 (human) and sno-412 (mouse) that was employed for the normalization of the expression level of miR-499.

Example 3

MiR-499 Translocates from Neighboring Cells to Cardiac Stem Cells Through Gap Junctions Engraftment of hCSCs in proximity of the infarct is the initial fundamental process of tissue repair. Engraftment requires the expression of surface proteins involved in cell-to-cell contact and the connection between cells and the interstitium. This process is characterized by the formation of gap and adherens junctions between CSCs and neighboring cells. Intercellular communication is critical for the survival of homed cells in the hostile milieu of the ischemic myocardium; also it appears to have other important functions (Bearzi et al., 2007; Urbanek et al., 2006; and Rota et al., 2007). Similar cell-to-cell interactions are present in the intact myocardium where this intercellular system may condition the fate of progenitor cells by influencing their state of quiescence, proliferation or lineage commitment. hCSCs are organized in clusters and form gap and adherens junctions with myocytes and fibroblasts which operate as supporting cells within cardiac stem cell niches (Urbanek et al., 2006).

Intercellular communications allow individual cells of an organism to accomplish their function in a coordinated manner in multicellular organs and tissues (Vinken et al., 2006; Hervé et al., 2007; and Meşe et al., 2007). Specifically, gap junctional communications rely on intercellular protein channels, which span the lipid bi-layers of contiguous cells and permit the direct exchange of ions and small molecules (Söhl and Willecke, 2004; Peters, 2006; Loewenstein, 1981; and Neijssen et al., 2005). Molecules of approximately 1.0-1.5 kDa were thought to represent the upper limit for permeation through gap junction channels (Loewenstein, 1981; and Neijssen et al., 2005). The recent documentation that synthetic oligonucleotides with molecular weights of 2-4 kDa can traverse gap junction channels made by connexin 43 has raised the intriguing possibility of a novel modality of intercellular control of gene expression (Valiunas et al., 2005; Wolvetang et al., 2007; and Todorova et al., 2008). Short RNAs translocate between mouse, rat and human cells in different in vitro systems (Valiunas et al., 2005), including human embryonic stem cells (Wolvetang et al., 2007; and Todorova et al., 2008).

The presence of gap junctions between cells of different type, i.e. cardiomyocytes and hCSCs, suggests that gap junctions provide a pathway for the passage of information from differentiated cells to progenitor cells. Deletion of connexin 43 in osteoblasts and stromal cells of the bone marrow results in severe defects in hematopoiesis indicating that gap junctions play a crucial role in blood cell generation in embryonic and post-natal life (Cancelas et al., 2000; Montecino-Rodriguez and Dorshkind, 2001; and Rosendaal and Jopling, 2003). Deficiency of connexin 43 induces a maturation arrest of long-term repopulating hematopoietic stem cells (HSCs), which show an impaired ability to proliferate and differentiate (Cancelas et al., 2000; Montecino-Rodriguez and Dorshkind, 2001; and Rosendaal and Jopling, 2003). Thus, in the bone marrow niches, a cross-talk occurs through gap junctions between HSCs and supporting cells. However, the molecules involved in this intercellular communication are currently unknown. Human embryonic stem cells (ESCs) express in vitro most of human connexin genes and form functionally-competent gap junction channels (Todorova et al., 2008; and Huettner et al., 2006), suggesting that coupling between ESCs may play a role in coordinating cellular responses that maintain pluripotency or stimulate differentiation.

The possibility of miR traffic through gap junction channels has provided an additional level of complexity to the notion of intercellular communication. We have demonstrated that CSCs and their committed progeny vary in miR profiling (Example 1) and this difference is the prerequisite for an efficient transfer of miRs from the donor to the recipient cell. The translocation of miR-499 from cardiomyocytes to CSCs imposes significant changes in gene expression in the primitive cell. In this regard, miRs are attractive candidates for the control of stem cell self-renewal and fate decision, because of their ability to regulate simultaneously many targets providing a way for the coordinated control of multiple genes and the rapid repression of several transcripts (Alvarez-Garcia and Miska, 2005; Chapman and Carrington, 2007; and Chu and Rana, 2007). During differentiation, hCSCs have to downregulate stem cell maintenance genes and activate lineage-specific genes (Beltrami et al., 2003; Urbanek et al., 2005; Linke et al., 2005; Smith et al., 2007; and Bearzi et al., 2007). We have identified target genes of miR-499, including Sox5, Sox6 and Rod1, that may need to be repressed to allow lineage specification and determination of hCSCs (Example 2). Thus, hCSC differentiation into myocytes and their acquisition of the adult phenotype may be regulated by the surrounding cells by the translocation of miR-499 through gap junctions.

Figure 6A:
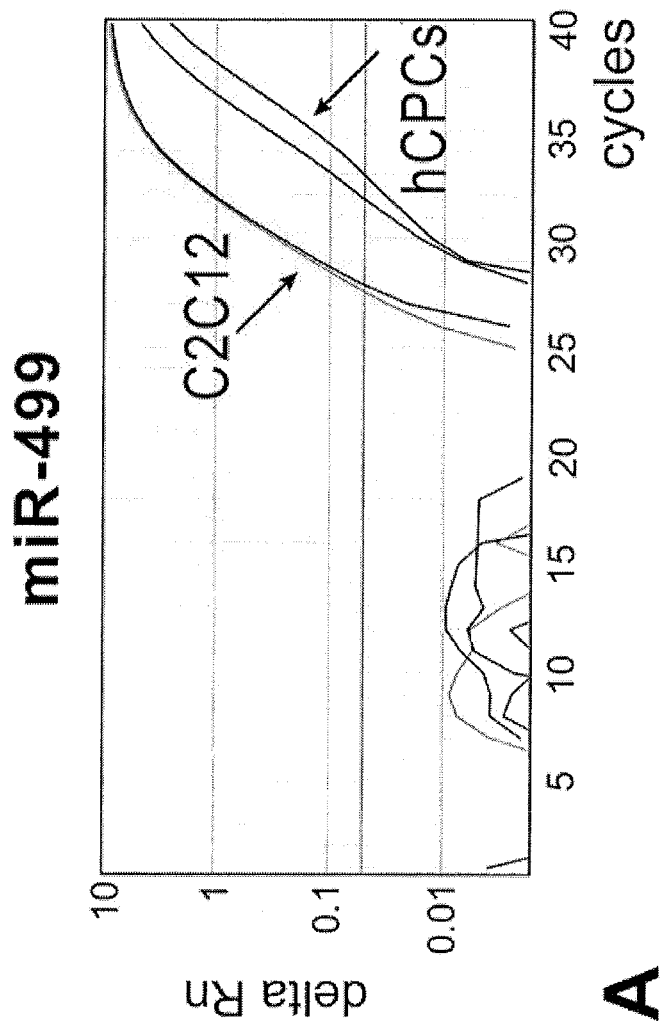
FIG. 6. A. Quantitative RT-PCR for miR-499 in C2C12 myoblasts and hCSCs. The quantity of miR-499 is higher in C2C12 myoblasts than hCSCs. B, C. After 24 hours, miR-499 (red) was present in hCSCs (c-kit, green) co-cultured with C2C12. Connexin 43 (white) was expressed at the interface between the two cell types.

Two series of experiments were performed to test whether miR-499 could traverse gap junctions. In a first series of experiments, C2C12 myoblasts, which express miR-499 (FIG. 6A), were co-cultured with recipient hCSCs. The presence of miR-499 in hCSCs was documented by quantitative fluorescence in situ hybridization (Q-FISH) utilizing a Locked-Nucleic Acid (LNA) probe which forms a stable complex with the target molecule. After 24 hours, the majority of hCSCs, which are recognized by the expression of c-kit on their plasma membrane, contained miR-499 (FIG. 6 B,C). The presence of connexin 43 at the interface between C2C12 myoblasts and hCSCs indicates the formation of gap junctions.

Figure 7:
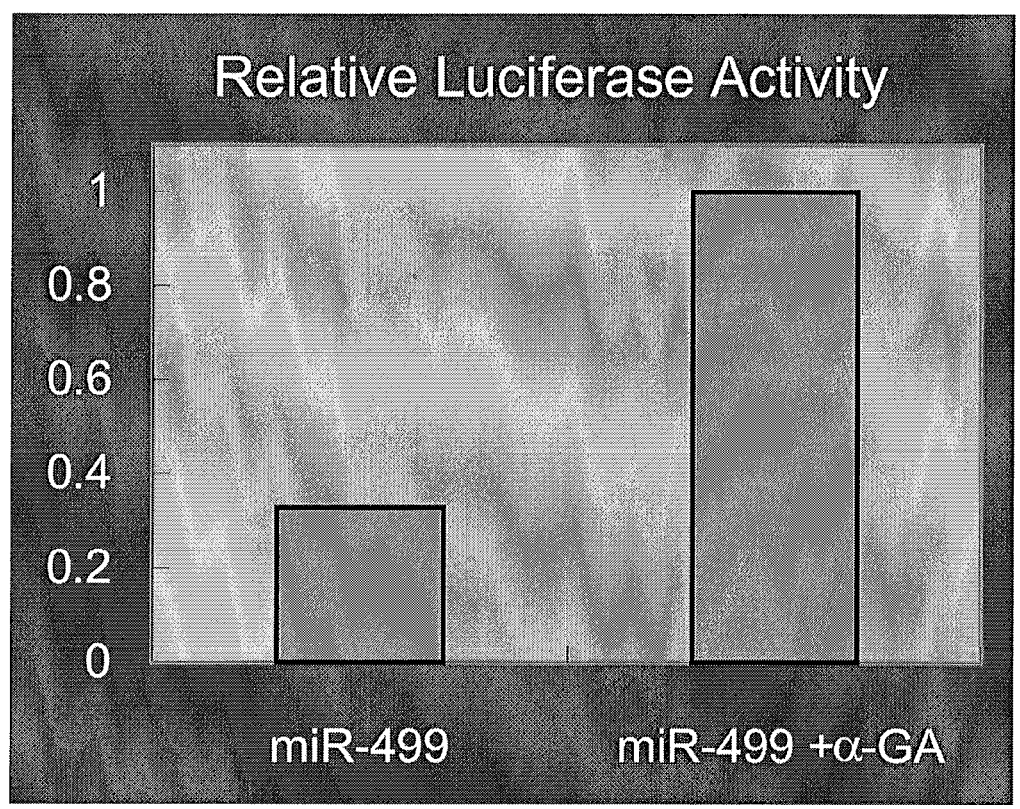
FIG. 7. Effect of the translocated miR-499 on the 3'-UTR of the Sox6 gene measured by the luciferase reporter assay. This function of miR-499 was abolished when co-cultures were treated with the gap junction inhibitor α-GA.
Figure 8D:
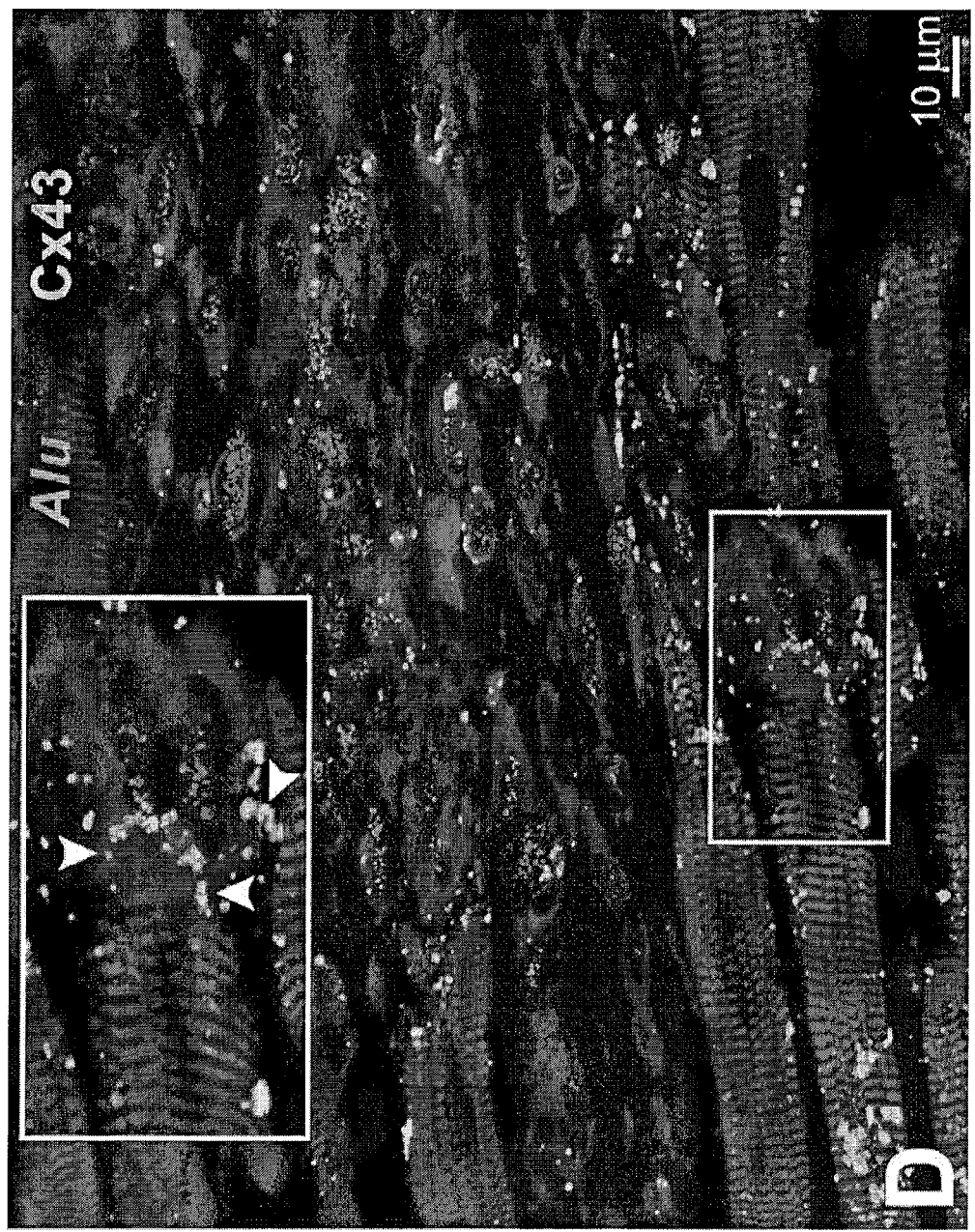
FIG. 8. A-C. Human myocardial niche containing 14 c-kit positive CSCs (A, green). Arrows delimit the areas shown in panels B and C. Connexin 43 and N-cadherin are expressed between CSCs and between CSCs and fibroblasts (procollagen, blue) and myocytes (α-sarcomeric actin, red). D. Area of myocardial regeneration in the rat heart following the injection of human CSCs. Newly formed Alu-positive human myocytes are interconnected with Alu-negative rat myocytes by connexin 43.

In a second series of experiments, a reporter assay was developed to measure the functional competence of miR-499 in hCSCs after its translocation from neighboring donor cells. Distinct populations of hCSCs were prepared. One pool of hCSCs served as donor cells and was transfected with an expression vector carrying miR-499 under the control of the CMV promoter (CMV-miR-499); hCSCs transfected with empty plasmid (CMV-blank) were used as negative control donor cells. A second pool of hCSCs, which served as recipient cells, was transfected with a reporter plasmid carrying the luciferase coding sequence and the 3'-UTR of the Sox6 gene (see Example 2). Donor and recipient cells were co-cultured for 3 days in the absence or presence of the gap junction inhibitor 18α-Glycyrrhetinic Acid (α-GA) (Wolvetang et al., 2007; Davidson et al., 1986; and Takeda et al., 2005). A β-gal-expressing plasmid was employed to normalize luciferase activity. Luciferase activity was found to be significantly decreased in recipient cells co-cultured with donor cells carrying the miR-499 plasmid when the hCSCs were exposed to α-GA (FIG. 7). The data from these two series of experiments suggest that functional mature miR-499 translocate into hCSCs through gap junction channels made by connexin 43. The observation of in vitro gap junction formation between CSCs and neighboring cells is consistent with observations made in the human heart in situ and following the injection of hCSCs in the infarcted mouse or rat heart (FIG. 8; Bearzi et al. 2007; and Hosoda et al. 2008).

Specific Methods

Q-FISH for miR-499.

A digoxygenin-labeled Locked Nucleic Acid (LNA) probe (Exiqon) complementary to mature miR-499 was utilized. hCSCs were fixed in 4% paraformaldehyde. After washing in RNase free PBS, cells were treated with proteinase K (500 ng/ml) followed by incubation in 0.2% glycine for 30 sec and washing with RNase-free water. Samples were pre-hybridized for 2 hours in hybridization buffer (50% formamide, 5×SSC, 0.4% Tween, 9.2 mM citric acid [ph 6.0], 50 µg/ml heparin, 500 µg/ml yeast RNA). Cells were hybridized overnight in the presence of 20 nM digoxigenin-labeled probe at 21° C. Samples were washed twice in 2×SSC at 37° C. followed by high stringency wash in 50% formamide, 2×SSC at hybridization temperature (Bearzi et al. 2007; and Rota et al. 2007). Immunological detection was carried out with anti-digoxigenin Fab conjugated to rhodamine. Negative controls consisted of omission of the LNA probe and use of a scrambled probe that had very low homology with the target sequence. Adult and neonatal myocytes were used as positive controls.

MiR-499 Transfer.

Three approaches are employed to demonstrate that functionally competent miR-499 translocates from neighboring cells to hCSCs via gap junctions.

a) Real-Time Transfer of miR-499.

Translocation of miR-499 through gap junctions is studied in living cells by two-photon microscopy. Thus, we labeled the 5'-side of mature miR-499 (21 nucleotides) with the fluorescent dye Cy3. 3T3 fibroblasts are transfected with Cy3-miR-499 and used as donor cells; EGFP-positive hCSCs are employed as recipient cells. Cy3-miR-499 is utilized at a final concentration of 30 nM in OPTI-MEM (Invitrogen) containing 8 µl of the transfection agent NeoFx (Applied Biosystems). Following 10 minutes of incubation, growth medium (DMEM, 10% FBS) is placed in 60-mm Petri dishes in which 3T3 cells ($5×10^5$ cells/dish) are plated overnight. The following day 3T3 cells are carefully washed with PBS to remove free Cy3-miR-499 and fresh medium is added. EGFP-positive hCSCs ($5×10^5$ cells/dish) are co-cultured with 3T3 cells in the presence of Alexa647-conjugated connexin 43 antibody. One hour later, Petri dishes are placed under the stage of a two-photon microscope and studied for 8 hours. Images are taken 20 min apart. Alexa647-conjugated connexin 43 antibody allows the detection of the expression of connexin 43 at the interface between adjacent cells in living cells. Since Cy3-miR-499 cannot leave the cells, the presence of red fluorescence in EGFP-positive hCSCs is indicative of the transfer of miR-499 through gap junctions from 3T3 cells.

This is confirmed by the use of the gap junction inhibitor α-GA, 10 µM. At the end of the experiment, EGFP-positive hCSC are sorted by FACS and RNA is extracted using mir-Vana kit. Quantitative RT-PCR for miR-499 (see Example 2 for specific methods) is performed to establish the translocation of full-length miR-499 through gap junctions. hCSCs co-cultured with non-transfected 3T3 cells are used to assess endogenous miR-499.

b) Translocation of Full-Length miR-499.

Neonatal rat ventricular myocytes are employed as donor cells and EGFP-positive hCSCs as recipient cells. Co-culture of myocytes and hCSCs is done in 4-well culture slides at a ratio of 10:1. Three days later, cells are fixed to perform Q-FISH for miR-499 (see methods above). In an additional set of experiments, at the end of the 3-day period, EGFP-positive hCSCs are sorted by FACS and utilized for quantitative RT-PCR. Again, the gap junction inhibitor α-GA is used to confirm that miR-499 translocation occurs through gap junctions.

c) Translocation of Functionally Competent miR-499.

3T3 fibroblasts are transfected with a plasmid in which a murine genomic DNA fragment of 254 bp including miR-499 was cloned downstream of the CMV promoter (CMV-miR-499). hCSCs are transfected with reporter plasmids containing the 3'-UTR sequences of the genes Sox5, Sox6 and Rod1 ligated at a position downstream the luciferase coding sequence (see Example 2 for specific methods). 3T3 cells overexpressing miR-499 are employed as donor cells and hCSCs expressing luciferase as recipient cells. Donor 3T3 cells are plated at a density of $2 \times 10^4$ cells in each well of a 6-well dish and transfected with 1 µg of CMV-miR-499 or CMV-blank. Recipient hCSCs are plated at a density of $5 \times 10^3$ cells in each well of a 6-well dish and transfected with 0.9 µg each of CMV-Luci-Sox5-UTR, CMV-Luci-Sox6-UTR or CMV-Luci-Rod1-UTR. A CMV-β-Gal plasmid, 0.1 µg, is used for normalization of luciferase activity. Six hours later, cells are washed in PBS three times. Recipient transfected cells are trypsinized and plated together with donor cells at a ratio of 4:1 for 4 days. Cells are incubated in lysis buffer and luciferase activity is measured. hCSCs transfected with the same reporter plasmids but cultured with non-transfected 3T3 are used as baseline. Downregulation of luciferase activity in co-cultured cells is indicative of translocation of miR-499 to hCSCs. The gap junction inhibitor α-GA will be added in a separate set of experiments to confirm the translocation of miR-499 is via the gap junctions.

Example 4

MiR-499 Promotes the Differentiation of Cardiac Stem Cells into Cardiomyocytes

In this example, two approaches are employed to document the function of miR-499, Sox6 and Rod1 in rat and human CSCs. In a first series of experiments, hCSCs were transfected with an expression vector carrying miR-499 under the control of the CMV promoter (CMV-miR-499) and markers of cell proliferation and myocyte differentiation were evaluated three days later by quantitative RT-PCR and immunocytochemistry. Following transfection, the quantity of miR-499 in hCSCs increased 3.000-fold (FIG. 9A, B). BrdU incorporation decreased 60% in hCSCs transfected with miR-499 compared to hCSCs transfected with an empty vector (FIG. 9C). hCSCs expressing miR-499 also displayed a marked upregulation of the myocyte-specific transcription factors Nkx2.5 and MEF2C at the mRNA level (FIG. 9D). In a second series of experiments, Sox6 and Rod1 were selectively blocked in rat CSCs with siRNA technique (see Example 2 for description of Sox6- and Rod-1 siRNA). When CSCs were transfected with Sox6-siRNA, mRNA expression of Sox6 was 86% lower than in non-transfected controls (FIG. 9E). Similarly, Rod1 mRNA was 50% lower when CSCs were transfected with Rod1-siRNA (FIG. 9E). In both cases, three days after siRNA transfection, the fraction of CSCs committed to the myocyte lineage increased significantly in agreement with the biochemical results. In comparison with CSCs exposed to random siRNA, the percentage of Nkx2.5-positive and MEF2C-positive cells increased 2-3-fold in the presence of siRNA against Sox6 and Rod1 (FIG. 9F). These data suggest that Sox6 and Rod1 are novel target genes of miR-499 and that inhibition of the expression of Sox6 and Rod1 promotes the differentiation of CSCs into cardiomyocytes.

Specific Methods

Function of miR-499 in hCSCs.

The effects of miR-499 on the growth of hCSCs was established by transfection with an expression plasmid carrying miR-499. Proliferation and differentiation of hCSCs was evaluated by immunocytochemistry, quantitative RT-PCR and Western blotting.

a) Transfection of hCSCs with Expression Plasmid CMV-miR-499.

Three µl of transfection reagent XP-1 (Applied Biosystems) was added to 100 µl of OPTI-MEM and after a 10 min-incubation was mixed to the plasmids CMV-miR-499 or CMV-blank, 1 µg. After 10 min, the solution containing the plasmids was added to hCSCs in vitro. The medium was removed after 6 hours and replaced with fresh medium. Cells were cultured for three days. BrdU, 1 µg/ml, was added twice a day during the duration of experiment. Cells were employed for immunocytochemistry and molecular biology studies.

b) Immunocytochemistry.

Transfected cells were fixed in 4% paraformaldehyde. To assess the degree of proliferation of transfected hCSCs, samples were stained with BrdU monoclonal antibody. The fraction of hCSCs positive for the cell cycle markers Ki67 and MCM5 was also measured. To evaluate the lineage commitment of hCSCs in culture, antibodies for transcription factors and cytoplasmic proteins specific for myocytes were included: Nkx2.5, MEF2C, GATA4, α-sarcomeric actin, α-cardiac actinin, troponin I, troponin T, and cardiac myosin heavy chain (Kajstura et al., 1998; Beltrami et al., 2001; Limana et al., 2003; Urbanek et al., 2003; Urbanek et al., 2005; and Beltrami et al., 2003). The presence of apoptotic cells was quantitatively measured by TdT assay and hairpin 1 probe labeling (Urbanek et al., 2005; and Rota et al., 2006).

c) Luciferase Reporter Assay.

This assay required co-transfection of hCSCs with CMV-miR-499 and luciferase reporter plasmids for Sox5, Sox6 or Rod1. hCSCs were co-transfected with 0.1 µg of luciferase reporter plasmid, 0.1 µg of β-gal control plasmid, and CMV-miR-499 or CMV-blank. Different amounts of CMV-miR-499 varying from 0.1 µg to 0.8 µg were used to confirm that the translational inhibition of luciferase is dose-dependent. A luciferase reporter plasmid without the addition of 3'-UTR was employed as a negative control (Boni et al., 2008).

d) Quantitative RT-PCR.

Total RNA was extracted from CMV-miR-499 and CMV-blank transfected hCSCs with mirVana miRNA isolation kit (Applied Biosystems) and employed for the measurement of miR-499 expression as well as the quantity of the transcripts for Sox5, Sox6, Rod1 (the target genes of miR-499) and Nkx2.5, MEF2C, myocardin and GATA4 (myocyte markers). Human myocardium was employed as a positive control. cDNA for mRNAs was obtained from 1 µg total RNA in a 20

µl reaction containing first strand buffer, 0.5 mM each of dTTP, dATP, dGTP and dCTP together with 200 U of Superscript III (Invitrogen), 40 U of Rnase inhibitor (Rnasin Plus, Promega) and 50 pmole of oligo(dT)15 primer (Bearzi et al., 2007; and Gonzalez et al., 2008). This mixture was incubated at 42° C. for 2 hours. Subsequently, real-time RT-PCR was performed with the following primers designed using the Primer Express v2.0 (Applied Biosystems) or Vector NTI (Invitrogen) software. "F" designates the forward primer and "R" designates the reverse primer.

```
hSox5-F:
                              (SEQ ID NO.: 27)
5'-AGC TTT TTG CCA TCC ACC AGG-3' hSox5-R:
                              (SEQ ID NO.: 28)
5'-ATA ACA GGC ATC CCA GGC TCT -3' hSox6-F:
                              (SEQ ID NO.: 29)
5'-CCG ACA TGC ATA ACT CCA ACA T -3' hSox6-R:
                              (SEQ ID NO.: 30)
5'-CGG TCG GGG TTT GTA TTT ATA GTT-3' hRod1-F:
                              (SEQ ID NO.: 31)
5'-GTC CAA ACA TCA AGC AGT ACA GC-3' hRod1-R:
                              (SEQ ID NO.: 32)
5'-AGA TCA TCC ACT GTA ACA GAA GGG -3' hNkx2.5-F:
                              (SEQ ID NO.: 33)
5'-TCT ATC CAC GTG CCT ACA GCG -3' hNkx2.5-R:
                              (SEQ ID NO.: 34)
5'-GCT CCA GCT CAT AGA CCT GCG-3' hMEF2C-F:
                              (SEQ ID NO.: 35)
5'-TGG TGT AAC ACA TCG ACC TCC AAG-3' hMEF2C-R:
                              (SEQ ID NO.: 36)
5'-TCA AGT TAC CAG GTG AGA CCA GCA-3' hGata4-F:
                              (SEQ ID NO.: 37)
5'-GGA GAT GCG TCC CAT CAA GAC-3' hGata4-R:
                              (SEQ ID NO.: 38)
5'-GGA GAC GCA TAG CCT TGT GG-3' hMyocardin-F:
                              (SEQ ID NO.: 39)
5'-AGA AGG GCA CAG GGT CTC CT-3' hMyocardin-R:
                              (SEQ ID NO.: 40)
5'-ACT CCG GGT CAT TTG CTG CT-3' hActb-F:
                              (SEQ ID NO.: 41)
5'-AAG ATC AAG ATC ATT GCT CCT CCT G-3' hActb-R:
                              (SEQ ID NO.: 42)
5'-CGG ACT CGT CAT ACT CCT GCT-3'
```

The 7300 Real-Time PCR system (Applied Biosystems) was employed for quantitative RT-PCR that was performed in duplicate. In each case, cDNA synthesized from 50 ng total RNA was used. cDNA was combined with Power SYBR Green master mix (Applied Biosystems) and 0.5 µM each of forward and reverse primers. Cycling conditions were as follows: 95° C. for 10 min followed by 40 cycles of amplification (95° C. denaturation for 15 sec, and 60° C. annealing-extension for 1 min). The melting curve was then obtained. To avoid the influence of genomic contamination, forward and reverse primers for each gene were located in different exons. Reactions containing cDNA generated without reverse transcriptase and reactions with primers alone were also included. PCR efficiency was evaluated using a standard curve of four serial dilution points. Quantified values were normalized against the input determined by the housekeeping gene β-actin (Actb). Real-time PCR products were run on 2% agarose/1×TBE gel. Amplified fragments were cut out and DNA was extracted using QIAquick Gel Extraction kit (Qiagen). DNA was eluted in 30 µl of 10 mM Tris buffer (pH 8.5), and amplified by Platinum Blue PCR Supermix (Invitrogen) in the presence of 260 nM of the forward and reverse primers utilized for real-time PCR. PCR reaction was carried out in Eppendorf Mastercycler (Bearzi et al., 2007; and Gonzalez et al., 2008). Cycling conditions were as follows: 94° C. for 2 min followed by 35 cycles of amplification (94° C. denaturation for 20 sec, 60° C. annealing for 30 sec, 72° C. elongation for 20 sec) with a final incubation at 72° C. for 3 min. After purification using QIAquick PCR Purification kit (Qiagen), samples were submitted to the DNA Sequencing Facility (Dana Farber, Boston).

e) Western Blotting.

Proteins from CMV-miR-499 and CMV-blank transfected hCSCs were extracted using M-PER Mammalian Protein Extraction Reagent (Pierce Biotechnology) and protease inhibitors. Protein concentration was measured by Bradford assay (Bio-Rad). Equivalents of 30 µg protein was separated on 8-12% SDS-PAGE. Proteins were subsequently transferred onto nitrocellulose membranes, blocked with 5% BSA or 5% dry skim milk in Tris-saline buffer with 0.1% Tween20 (TBST) for 1 h at room temperature, and exposed to rabbit polyclonal anti-Sox5 (Santa Cruz), rabbit polyclonal anti-Sox6 (Sigma), goat polyclonal anti-Rod1 (Santa Cruz), rabbit polyclonal anti-Nkx2.5 (Santa Cruz) and goat polyclonal anti-MEF2C diluted 1:2000-1:200 in TBST overnight at 4° C. HRP-conjugated IgG was used as secondary antibodies (Pierce Biotechnology). Proteins were detected by chemiluminesence (SuperSignal West Femto Maximum Sensitivity Substrate, Pierce Biotechnology) and OD was measured (Urbanek et al., 2005a; Urbanek et al., 2005b; Boni et al. 2008; and Gonzalez et al., 2008). Loading conditions were determined by the expression of β-actin (Sigma). Human myocardium was employed as a positive control.

Example 5

MiR-499 May Promote CSC Differentiation by Activation of the WNT/β-Catenin Pathway Numerous downstream effector pathways may mediate the function of Sox5, Sox6 and Rod1. We have elected to test whether the preservation of the primitive state of hCSCs is regulated by inhibition of the Wnt pathway while the maturation of hCSCs and the formation of functionally competent myocytes require the stabilization of β-catenin by Wnt ligands. Specifically, active Wnt is believed to be essential for the late stages of maturation of hCSCs into myocytes and the transition from the highly proliferative state of transit amplifying cells to the quiescence of terminally differentiated cardiomyocytes.

Wnts are a family of secreted proteins composed of numerous isoforms (Willert et al., 2003; and Nusse et al., 2003). Two types of receptors mediate the Wnt activity: the Frizzled receptor that is a seven transmembrane pass-protein and the low-density lipoprotein receptor-related proteins (LRP) (Wang and Malbon, 2003; and Fujino et al., 2003). The main downstream event of the Wnt cascade is the stabilization of β-catenin (Daniels et al., 2001). In the absence of Wnt, β-catenin is phosphorylated by GSK-3β and in part degraded through the ubiquitin-proteasome pathway. However, part of β-catenin participates in the generation of adherens junctions with E-cadherin, mediating cell-to-cell adhesion and hCSC homing and quiescence within the myocardium (Urbanek et al., 2006; and Gottardi and Gumbiner, 2001). Conversely, when β-catenin is stabilized by Wnt and accumulates in the cytoplasm, a significant portion of β-catenin is translocated to the nucleus where it confers the property of transcription factors to the Lef/TCF family of DNA binding proteins (Huber et al., 1996). Lef/TCF proteins associate with a number of chromatin-remodeling factors that activate or repress target genes (Hsu et al., 1998; and Novak and Dedhar, 1999).

During development, the Wnt/β-catenin pathway plays a biphasic role, positive and negative, in controlling differentiation of cardiomyocytes (Naito et al., 2006; and Kwon et al., 2007). At different stages of cardiac morphogenesis, this axis has distinct and even opposing functions, playing a critical inhibitory role in the initial formation of cardiovascular progenitors and later acting as a positive signal for cell commitment (Naito et al., 2006; Kwon et al., 2007; and Nakamura et al., 2003). Both canonical and non-canonical Wnt have been shown to favor the commitment of progenitor cells to myocytes (Koyanagi et al., 2005; and Koyanagi et al., 2007). The upregulation of miR-499 in hCSCs may repress Sox5 and Sox6 favoring the function of Sox7, Sox17 and Sox18, which in turn activate the Wnt/β-catenin pathway, initiating myocyte differentiation. By applying siRNA technique, it has been documented that Sox17 promotes the expression of cardiogenic transcription factors, such as Nkx2.5, Mef2C, Tbx5 and myocardin (Liu et al., 2007). The members of the SoxF subfamily, i.e. Sox7, Sox17 and Sox 18, may have redundant roles in cardiovascular development (Sakamoto et al., 2007); however, Sox5 and Sox6 may antagonize the function of the three SoxF proteins. During endodermal development, Sox17 is bound to β-catenin and the formation of this complex potentiates the transcriptional activation of target genes (Liu et al., 2007).

This Example outlines experiments that test the function of miR-499 target genes (e.g. Sox5, Sox6, and Rod1) in hCSCs and their interaction with Wnt/β-catenin pathway. In a first series of experiments, the effects of Sox5, Sox6 and Rod1 on the growth of hCSCs are established by a gain and loss of function approach. Transfection of hCSCs with Sox5-siRNA, Sox6-siRNA and Rod1-siRNA is expected to promote differentiation of hCSCs in a manner similar to mi-R499 overexpression. However, transfection with single siRNA allows us to establish the consequences of the repression of each gene on proliferation and commitment of hCSCs. Opposite results are expected when hCSCs are transfected with expression plasmids carrying Sox5, Sox6 and Rod1 (see Example 2 for description of expression plasmids) with preservation of the undifferentiated state of hCSCs being observed. Transfected cells are employed for immunocytochemistry and molecular biology studies (see Example 4).

In a second series of experiments, the effects of overexpressing miR-499 in hCSCs on Sox17 and its interaction with β-catenin will be examined. To demonstrate the physical interaction between β-catenin and Sox17 (Sinner et al., 2004) in nuclei of hCSCs overexpressing miR-499, immunoprecipitation and Western blotting are performed (Urbanek et al., 2005a; Urbanek et al., 2005b; Boni et al. 2008; and Gonzalez et al., 2008). Nuclear protein lysates are obtained from hCSCs overexpressing miR-499 and pulled-down with rabbit anti-β-catenin polyclonal antibody (Santa Cruz). Western blotting is performed with mouse anti-Sox17 monoclonal antibody (R&D Systems), 1:2000, to detect the protein complex. The presence of a complex between Sox17 and β-catenin in the nucleus of cells overexpressing miR-499 is expected.

Example 6

Myocardial Regeneration by Cardiac Stem Cells Overexpressing miR-499

The objective of this Example is to test whether the in vitro observations concerning the positive role of miR-499 on hCSC differentiation have a functional counterpart in vivo. To address this question, hCSCs overexpressing miR-499 will be administered to the infarcted heart to determine if myocardial regeneration with formation of mature functionally competent cardiomyocytes is induced.

As expected, downregulation of miR-499 may interfere with the function of numerous cardiomyogenic factors, such as SoxF proteins and the Wnt-β-catenin pathway. In differentiating hCSCs, a limited or delayed upregulation of miR-499 is expected to be associated with the arrest of myocyte differentiation at an early stage of commitment. Under this condition, a large number of transient amplifying myocytes is formed. These cells have high proliferative capacity, are small in size and contain a little amount of myofibrils located at the periphery of the cytoplasm. Transit amplifying myocytes are characterized by a prolonged expression of the early myocyte transcription factor Nkx2.5, which can interfere with the appearance of late markers of cardiomyogenesis such as GATA4 (Boni et al., 2008). This cellular behavior would conform to a model of differentiation delay in which the persistence of Sox5, Sox6 and Rod1 opposes the progression of myocyte maturation. Forced expression of miR-499 in hCSCs, which would downregulate Sox5, Sox6, and Rod1 favoring myocyte maturation, may enhance the regenerative capacity of this pool of primitive cells favoring their clinical implementation.

hCSCs are infected with a lentiviral vector carrying miR-499 and are injected in the border zone of immunosuppressed infarcted rats. This strategy is implemented in an attempt to counteract the defective differentiation of hCSCs (Bearzi et al., 2007; and Hosoda et al., 2008), which may be mediated by the lack of miR-499 in the implanted hCSCs. This molecular modification may promote the transition of hCSCs from early to late myocyte differentiation.

Infarcted animals treated with EGFP-labeled hCSCs overexpressing miR-499 are sacrificed at different time points after coronary ligation and cell implantation and EGFP-positive myocytes are isolated from the regenerating myocardium to determine their molecular and immunocytochemical characteristics (Urbanek et al., 2005b; Bearzi et al., 2007; Gonzalez et al., 2008; and Rota et al., 2007). Also, the mechanical and electrical behavior of the regenerated myocytes is measured together with calcium transients (Beltrami et al., 2003; Urbanek et al., 2005b; Rota et al., 2007a; and Rota et al., 2007b). These molecular, immunocytochemical and functional data allow us to define whether the presence of miR-499 conditions the ability of hCSCs to promote myocardial regeneration after infarction and whether the restored myocardium acquired adult characteristics. Upregulation of miR- 499 in hCSCs may enhance the extent of the regenerative response promoting a faster recovery. The ability to modulate the quantity and timing of miR-499 expression in hCSCs may be essential for therapies that aim to balance the expansion of the myocyte progenitor cell pool together with their differentiation.

Specific Methods

Lentivirus-miR-499.

For the in vivo studies, a lentiviral vector carrying miR-499 and EGFP is generated to obtain stable infection of hCSCs prior to their injection into the infarcted rat heart. The human genomic DNA fragment of the hMyh7b intron 20 including the hsa-miR-499 is amplified by PCR utilizing the following primers:

```
hsa-stem Eco1-F:
                                     (SEQ ID NO.: 43)
5'-CAA GGG AAT TCC CCA TCT GGG AGA CAG ACC CTC-3' hsa-stem Eco1-R:
                                     (SEQ ID NO.: 44)
5'-GAT GGG AAT TCC TTC GCT GTC TCC CAT CAC CAC-3'
```

The PCR product is ligated into a CGW plasmid vector carrying EGFP. The direction of insertion is confirmed by sequencing. HEK293T/17 cells cultured in DMEM, 10% FBS, are used as packaging cells for lentiviral production. Four plasmids are mixed and diluted in 1.5 ml OPTI-MEM: gag/pol, 6.5 µg, VSVG, 3.5 µg, pRSV-rev, 2.5 µg, and CGW-miR-499, 10 µg. Plasmids are then combined with Lipofectamine 2000 (Invitrogen). Twenty minutes later, this mixture is added to culture dishes. Six hours later, the medium is removed and fresh medium added. Medium is collected at 24 and 48 hours, and frozen after filtration.

Similar methods are used for preparation of lentiviral vectors carrying different microRNAs, such as miR-1, miR-133a, and miR-133b. For example, the following primers are used to amplify each of the specific miRNAs from human genomic DNA:

```
hsa-miR-1-Eco1-F:
                                     (SEQ ID NO.: 45)
5'-GAC GGG AAT TCA CGT AGA AAG AAG CAA GAG CT-3' hsa-miR-1-Eco1-R:
                                     (SEQ ID NO.: 46)
5'-TAC CAG AAT TCT ACA TTA GTA AGC TGA ATG TTT
C-3' hsa-miR-133a-Eco1-F:
                                     (SEQ ID NO.: 47)
5'-GAA GCG AAT TCT CCA TCG GGA CTG CTT GGT GGA
G-3' hsa-miR-133a-Eco1-R:
                                     (SEQ ID NO.: 48)
5'-CTC AGG AAT TCA CTT ACT TGG AGC TGA CCA CGT-3' hsa-miR-133b-Eco1-F:
                                     (SEQ ID NO.: 49)
5'-AAT GCG AAT TCT TTT TGC ATT ACA GGC TTA GAC-3' hsa-miR-133b-Eco1-R:
                                     (SEQ ID NO.: 50)
5'-TCT CTG AAT TCC TGG GAG CAT AAG AAT ATG GTG-3'
```

Following EcoR1 digestion, the PCR products are ligated into a CGW plasmid. The same procedures as described above for lentiviral vectors carrying miR-499 are followed to obtain the lentivirus with the desired microRNA.

Cell Preparation.

hCSCs are isolated from 5 myocardial samples obtained from male patients and transduced with a lentiviral vector expressing miR-499 and EGFP. An empty lentivirus obtained from CGW vector without insertion of miR-499 is used as a control.

Animals.

Myocardial infarction is induced in female Fischer 344 rats at 3 months of age by permanent coronary artery occlusion. Permanent coronary artery occlusion is performed in rats anesthetized with ketamine (150 mg/kg body weight, i.p.), acepromazine (1.0 mg/kg body weight, i.p.), and xylazine (6 mg/kg body weight, i.p.). The thorax is opened via the third costal space, the atrial appendage elevated, the left coronary artery is located, and a silk braided suture (6-0) is inserted around the vessel near the origin and the artery occluded. hCSCs are injected shortly after coronary artery inclusion. Four intramyocardial injections of 10,000 cells each are made at the two opposite sides of the border zone of the infarct. The chest is closed and pneumothorax reduced by negative pressure. Immunosuppressive treatment consists of cyclosporine (10 mg/kg body weight, i.p.).

One group of animals receives miR-499-overexpressing hCSCs and one group is injected with hCSCs infected with the empty vector. In both cases, hCSCs will be EGFP-positive. Myocardial regeneration is evaluated 3 months later. Immunosuppression with cyclosporin A is initiated at the time of cell administration and maintained throughout (Bearzi et al., 2007). Similarly, Alzet microsmotic pumps (2ML4) that release BrdU continuously for 4 weeks is implanted every month to determine differences in growth rates between animals treated with the different populations of hCSCs.

Echocardiography.

Echocardiography is performed two days after coronary occlusion and cell implantation. This analysis is repeated at 2 and 4 weeks and then monthly (Bearzi et al., 2007; Gonzalez et al., 2008).

Ventricular Hemodynamics.

Animals are anesthetized and the right carotid artery cannulated with a microtip pressure transducer catheter (Millar SPR-240). The catheter is advanced into the left ventricle for the evaluation of the ventricular pressures and + and − dP/dt. A four-channel 100 kHz 16-bit recorder with built-in isolated ECG amplifier (iWorks IX-214) is used to store signals in a computer utilizing LabScribe software. For morphological and immunohistochemical studies, the heart is arrested in diastole with $CdCl_2$ and the myocardium fixed by perfusion of the coronary vasculature with formalin. The left ventricular chamber is fixed at a pressure equal to the in vivo measured LVEDP. This procedure is important for the acquisition of anatomical data of heart size and shape under comparable conditions in all animals. For biochemical and physiological studies, transplanted rats are used for the isolation of the EGFP-positive progeny derived from the injected cells. The heart is minced in incubation buffer containing collagenase and EGFP-labeled cells are sorted by FACS.

Detection of EGFP and Human Genes.

Real-time RT-PCR: RNA is extracted and reverse transcribed into cDNA. Specific primers are designed for EGFP, Nkx2.5, MEF2C, myocardin, GATA4 and SRF.

Immunocytochemistry of Myocardial Regeneration.

This analysis includes examination of myocyte specific markers: Nkx2.5, MEF2C, GATA4, α-sarcomeric actin, α-cardiac actinin, troponin I, troponin T, and cardiac myosin heavy chain protein, connexin 43 and N-cadherin. The presence of EGFP and Alu is assessed in the differentiating myocytes to establish their human origin. Human-specific Alu repeat sequences are detected by in situ hybridization with a probe (Biogenex, San Ramon, Calif.). For detailed methods, see Bearzi et al., 2007.

Cardiac Anatomy, Myocyte Volume and Number.

After paraffin-embedding, three tissue sections equal in thickness and including the entire left ventricle (LV) and interventricular septum from the base to the apex of the heart, is obtained and stained with hematoxylin and eosin. The midsection is used to evaluate LV wall thickness and chamber diameter. Chamber volume is then calculated (Rota et al., 2007a; Gonzalez et al., 2008; and Rota et al., 2007b). Infarct size is assessed by the fraction of myocytes lost from the LV (Beltrami et al., 2003; Urbanek et al., 2005b; and Bearzi et al., 2007). The volume of regenerated myocardium is determined by measuring in each of the three sections the area occupied by the restored tissue and section thickness. The product of these two variables yields the volume of tissue repair in each section. Values in the three sections are added, and the total volume of formed myocardium is obtained. The volume of 150 newly formed myocytes is measured in each heart. Only longitudinally oriented cells with centrally located nuclei are included. The length and diameter across the nucleus is collected in each myocyte to compute cell volume, assuming a cylindrical shape (Urbanek et al., 2005b; and Bearzi et al., 2007; and Rota et al., 2007b).

Cell Fusion.

To evaluate whether cell fusion is involved in the formation of EGFP-positive myocytes, the presence of rat and human sex chromosomes is measured in EGFP-positive cells. This is done because male hCSCs are injected in female infarcted hearts. Sections are preheated and exposed to enzymatic digestion. After dehydration with ethanol, sections and Rat Chromosome X and Y Paint probe (Cambio) are denatured and hybridized. Nuclei are stained with DAPI (Urbanek et al., 2005b; Bearzi et al., 2007; Rota et al., 2007b; and Tillmanns et al., 2008).

Cellular Physiology.

EGFP-positive myocytes, the progeny of the implanted hCSCs, are obtained by enzymatic digestion from the infarcted-regenerated region of the heart. The functional competence of these cells is established. *Mechanics and Ca2+ transients*: Myocytes are stimulated by platinum electrodes. Changes in cell length are quantified by edge tracking. Simultaneously, Fluo 3-fluorescence is excited at 488 nm. Different rates of stimulation and different extracellular Ca2+ concentrations are examined (Beltrami et al., 2003; Urbanek et al., 2005b; and Rota et al., 2007b). *Electrophysiology*: Data are collected by means of whole cell patch-clamp technique in voltage- and current-clamp mode and by edge motion detection measurements. Voltage, time-dependence and density of L-type Ca2+ current is analyzed in voltage-clamp preparations. Additionally, the T-type Ca2+ current is assessed; this current is restricted to young developing myocytes (Rota et al., 2007b). Also, the relationship between cell shortening and action potential profile is determined in current-clamp experiments (Rota et al., 2007a; and Rota et al., 2007b).

REFERENCES

1. Anversa P, Leri A, Beltrami C A, Guerra S, Kajstura J: Myocyte death and growth in the failing heart. Lab Invest. 78:767-86, 1998
2. Anversa P, Leri A, Kajstura J, Nadal-Ginard B: Myocyte growth and cardiac repair. J Mol Cell Cardiol. 34:91-105, 2002
3. Anversa P, Leri A, Kajstura J: Cardiac regeneration. J Am Coll Cardiol. 47:1769-76, 2006
4. Kajstura J, Leri A, Finato N, Di Loreto C, Beltrami C A, Anversa P: Myocyte proliferation in end-stage cardiac failure in humans. Proc Natl Acad Sci USA. 95:8801-5, 1998
5. Beltrami A P, Urbanek K, Kajstura J, Yan S M, Finato N, Bussani R, Nadal-Ginard B, Silvestri F, Leri A, Beltrami C A, Anversa P: Evidence that human cardiac myocytes divide after myocardial infarction. N Engl J. Med. 344: 1750-7, 2001
6. Limana F, Urbanek K, Chimenti S, Quaini F, Leri A, Kajstura J, Nadal-Ginard B, Izumo S, Anversa P: bcl-2 overexpression promotes myocyte proliferation. Proc Natl Acad Sci USA. 99:6257-62, 2002
7. Urbanek K, Quaini F, Tasca G, Torella D, Castaldo C, Nadal-Ginard B, Leri A, Kajstura J, Quaini E, Anversa P: Intense myocyte formation from cardiac stem cells in human cardiac hypertrophy. Proc Natl Acad Sci USA. 100: 10440-5, 2003
8. Urbanek K, Torella D, Sheikh F, De Angelis A, Nurzynska D, Silvestri F, Beltrami C A, Bussani R, Beltrami A P, Quaini F, Bolli R, Leri A, Kajstura J, Anversa P: Myocardial regeneration by activation of multipotent cardiac stem cells in ischemic heart failure. Proc Natl Acad Sci USA. 102:8692-7, 2005a
9. Beltrami A P, Barlucchi L, Torella D, Baker M, Limana F, Chimenti S, Kasahara F I, Rota M, Musso E, Urbanek K, Leri A, Kajstura J, Nadal-Ginard B, Anversa P: Adult cardiac stem cells are multipotent and support myocardial regeneration. Cell. 114:763-76, 2003
10. Oh H, Bradfute S B, Gallardo T D, Nakamura T, Gaussin V, Mishina Y, Pocius J, Michael L H, Behringer R R, Garry D J, Entman M L, Schneider M D: Cardiac progenitor cells from adult myocardium: homing, differentiation, and fusion after infarction. Proc Natl Acad Sci USA. 100:12313-8, 2003
11. Pfister O, Mouquet F, Jain M, Summer R, Helmes M, Fine A, Colucci W S, Liao R: CD31– but Not CD31+ cardiac side population cells exhibit functional cardiomyogenic differentiation. Circ Res. 97:52-61, 2005
12. Urbanek K, Rota M, Cascapera S, Bearzi C, Nascimbene A, De Angelis A, Hosoda T, Chimenti S, Baker M, Limana F, Nurzynska D, Torella D, Rotatori F, Rastaldo R, Musso E, Quaini F, Leri A, Kajstura J, Anversa P: Cardiac stem cells possess growth factor-receptor systems that after activation regenerate the infarcted myocardium, improving ventricular function and long-term survival. Circ Res. 97:663-73, 2005b
13. Linke A, Muller P, Nurzynska D, Casarsa C, Torella D, Nascimbene A, Castaldo C, Cascapera S, Bohm M, Quaini F, Urbanek K, Leri A, Hintze T H, Kajstura J, Anversa P: Stem cells in the dog heart are self-renewing, clonogenic, and multipotent and regenerate infarcted myocardium, improving cardiac function. Proc Natl Acad Sci USA. 102: 8966-71, 2005
14. Smith R R, Barile L, Cho H C, Leppo M K, Hare J M, Messina E, Giacomello A, Abraham M R, Marbán E: Regenerative potential of cardiosphere-derived cells expanded from percutaneous endomyocardial biopsy specimens. Circulation. 115:896-908, 2007
15. Bearzi C, Rota M, Hosoda T, Tillmanns J, Nascimbene A, De Angelis A, Yasuzawa-Amano S, Trofimova I, Siggins R W, Lecapitaine N, Cascapera S, Beltrami A P, D'Alessandro D A, Zias E, Quaini F, Urbanek K, Michler R E, Bolli R, Kajstura J, Leri A, Anversa P: Human cardiac stem cells. Proc Natl Acad Sci USA. 104:14068-73, 2007

16. Götz M, Huttner W B: The cell biology of neurogenesis. Nat Rev Mol Cell Biol. 6:777-88, 2005
17. Morrison S J, Kimble J: Asymmetric and symmetric stem-cell divisions in development and cancer. Nature. 441:1068-74, 2006
18. Watt F M: Epidermal stem cells: markers, patterning and the control of stem cell fate. Philos Trans R Soc Lond B Biol Sci. 353:831-7, 1998
19. Jones P H, Watt F M: Separation of human epidermal stem cells from transit amplifying cells on the basis of differences in integrin function and expression. Cell. 73:713-24, 1993
20. Watt F M, Hogan B L: Out of Eden: stem cells and their niches. Science. 287:1427-30, 2000
21. Taylor G, Lehrer M S, Jensen P J, Sun T T, Lavker R M: Involvement of follicular stem cells in forming not only the follicle but also the epidermis. Cell. 102:451-61, 2000
22. Wright N A: Epithelial stem cell repertoire in the gut: clues to the origin of cell lineages, proliferative units and cancer. Int J Exp Pathol. 81:117-43, 2000
23. Lansdorp P M: Role of telomerase in hematopoietic stem cells. Ann N Y Acad Sci. 1044:220-7, 2005
24. Flores I, Benetti R, Blasco M A: Telomerase regulation and stem cell behaviour. Curr Opin Cell Biol. 18:254-60, 2006.
25. Leri A, Kajstura J, Anversa P: Cardiac stem cells and mechanisms of myocardial, regeneration. Physiol Rev. 85:1373-416, 2005
26. Ramalho-Santos M, Yoon S, Matsuzaki Y, Mulligan R C, Melton D A: "Stemness": transcriptional profiling of embryonic and adult stem cells. Science. 298:597-600, 2002
27. Ivanova N B, Dimos J T, Schaniel C, Hackney J A, Moore K A, Lemischka I R: A stem cell molecular signature. Science. 298:601-4, 2002
28. Bruno L, Hoffmann R, McBlane F, Brown J, Gupta R, Joshi C, Pearson S, Seidl T, Heyworth C, Enver T: Molecular signatures of self-renewal, differentiation, and lineage choice in multipotential hemopoietic progenitor cells in vitro. Mol Cell Biol. 24:741-56, 2004
29. Bhattacharya B, Miura T, Brandenberger R, Mejido J, Luo Y, Yang A X, Joshi B H, Ginis I, Thies R S, Amit M, Lyons I, Condie B G, Itskovitz-Eldor J, Rao M S, Puri R K: Gene expression in human embryonic stem cell lines: unique molecular signature. Blood. 103:2956-64, 2004
30. Alvarez-Garcia I, Miska E A: MicroRNA functions in animal development and human disease. Development. 132:4653-62, 2005
31. Chapman E J, Carrington J C: Specialization and evolution of endogenous small RNA pathways. Nat Rev Genet. 8:884-96, 2007
32. Chu C Y, Rana T M: Small RNAs: regulators and guardians of the genome. J Cell Physiol. 213:412-9, 2007
33. Tijsterman M, Plasterk R H: Dicers at RISC; the mechanism of RNAi. Cell. 117:1-3, 2004
34. Gregory R I, Chendrimada T P, Shiekhattar R: MicroRNA biogenesis: isolation and characterization of the microprocessor complex. Methods Mol Biol. 342:33-47, 2006
35. Peters L, Meister G. Argonaute proteins: mediators of RNA silencing. Mol Cell. 26:611-23, 2007
36. Tuddenham L, Wheeler G, Ntounia-Fousara S, Waters J, Hajihosseini M K, Clark I, Dalmay T: The cartilage specific microRNA-140 targets histone deacetylase 4 in mouse cells. FEBS Lett. 580:4214-7, 2006
37. Saetrom P, Snøve O Jr, Rossi J J: Epigenetics and microRNAs. Pediatr Res. 61:17R-23R, 2007
38. Chuang J C, Jones P A: Epigenetics and microRNAs. Pediatr Res. 61:24R-29R, 2007
39. Yu B, Yang Z, Li J, Minakhina S, Yang M, Padgett R W, Steward R, Chen X: Methylation as a crucial step in plant microRNA biogenesis. Science. 307:932-5, 2005
40. Urbanek K, Cesselli D, Rota M, Nascimbene A, De Angelis A, Hosoda T, Bearzi C, Boni A, Bolli R, Kajstura J, Anversa P, Leri A: Stem cell niches in the adult mouse heart. Proc Natl Acad Sci USA. 103:9226-31, 2006
41. Söhl G, Willecke K. Gap junctions and the connexin protein family. Cardiovasc Res. 62:228-32, 2004
42. Peters N S: Gap junctions: clarifying the complexities of connexins and conduction. Circ Res. 99:1156-8, 2006
43. Loewenstein W R: Junctional intercellular communication: the cell-to-cell membrane channel. Physiol Rev. 61:829-913, 1981
44. Neijssen J, Herberts C, Drijfhout J W, Reits E, Janssen L, Neefjes J: Cross-presentation by intercellular peptide transfer through gap junctions. Nature. 434:83-8, 2005
45. Valiunas V, Polosina Y Y, Miller H, Potapova I A, Valiuniene L, Doronin S, Mathias R T, Robinson R B, Rosen M R, Cohen I S, Brink P R: Connexin-specific cell-to-cell transfer of short interfering RNA by gap junctions. J. Physiol. 568:459-68, 2005
46. Wolvetang E J, Pera M F, Zuckerman K S: Gap junction mediated transport of shRNA between human embryonic stem cells. Biochem Biophys Res Commun. 363:610-5, 2007
47. Todorova M G, Soria B, Quesada I: Gap junctional intercellular communication is required to maintain embryonic stem cells in a non-differentiated and proliferative state. J Cell Physiol. 214:354-62, 2008
48. Zhao Y, Samal E, Srivastava D: Serum response factor regulates a muscle-specific microRNA that targets Hand2 during cardiogenesis. Nature. 436:214-20, 2005
49. Zhao Y, Ransom J F, Li A, Vedantham V, von Drehle M, Muth A N, Tsuchihashi T, McManus M T, Schwartz R J, Srivastava D: Dysregulation of cardiogenesis, cardiac conduction, and cell cycle in mice lacking miRNA-1-2. Cell. 129:303-17, 2007
50. Sayed D, Hong C, Chen I Y, Lypowy J, Abdellatif M: MicroRNAs play an essential role in the development of cardiac hypertrophy. Circ Res. 100:416-24, 2007
51. Yang B, Lin H, Xiao J, Lu Y, Luo X, Li B, Zhang Y, Xu C, Bai Y, Wang H, Chen G, Wang Z: The muscle-specific microRNA miR-1 regulates cardiac arrhythmogenic potential by targeting GJA1 and KCNJ2. Nat Med. 13:486-91, 2007
52. Carè A, Catalucci D, Felicetti F, Bonci D, Addario A, Gallo P, Bang M L, Segnalini P, Gu Y, Dalton N D, Elia L, Latronico M V, Høydal M, Autore C, Russo M A, Dorn G W 2nd, Ellingsen O, Ruiz-Lozano P, Peterson K L, Croce C M, Peschle C, Condorelli G: MicroRNA-133 controls cardiac hypertrophy. Nat Med. 13:613-8, 2007
53. Tatsuguchi M, Seok H Y, Callis T E, Thomson J M, Chen J F, Newman M, Rojas M, Hammond S M, Wang D Z: Expression of microRNAs is dynamically regulated during cardiomyocyte hypertrophy. J Mol Cell Cardiol. 42:1137-41, 2007
54. van Rooij E, Olson E N: MicroRNAs: powerful new regulators of heart disease and provocative therapeutic targets. J Clin Invest. 117:2369-76, 2007
55. Berezikov E, Guryev V, van de Belt J, Wienholds E, Plasterk R H, Cuppen E: Phylogenetic shadowing and computational identification of human microRNA genes. Cell. 120:21-4, 2005

56. Bentwich I, Avniel A, Karov Y, Aharonov R, Gilad S, Barad O, Barzilai A, Einat P, Einav U, Meiri E, Sharon E, Spector Y, Bentwich Z: Identification of hundreds of conserved and nonconserved human microRNAs. Nat Genet. 37:766-70, 2005
57. Baskerville S, Bartel D P: Microarray profiling of microRNAs reveals frequent coexpression with neighboring miRNAs and host genes. RNA. 11:241-7, 2005
58. Nagase T, Kikuno R, Ishikawa K, Hirosawa M, Ohara O: Prediction of the coding sequences of unidentified human genes. XVII. The complete sequences of 100 new cDNA clones from brain which code for large proteins in vitro. DNA Res. 7:143-50, 2000
59. Desjardins P R, Burkman J M, Shrager J B, Allmond L A, Stedman H H: Evolutionary implications of three novel members of the human sarcomeric myosin heavy chain gene family. Mol Biol Evol. 19:375-93, 2002
60. Lefebvre V, Dumitriu B, Penzo-Méndez A, Han Y, Pallavi B: Control of cell fate and differentiation by Sry-related high-mobility-group box (Sox) transcription factors. Int J Biochem Cell Biol. 39:2195-214, 2007
61. Sinclair A H, Berta P, Palmer M S, Hawkins J R, Griffiths B L, Smith M J, Foster J W, Frischauf A M, Lovell-Badge R, Goodfellow P N: A gene from the human sex-determining region encodes a protein with homology to a conserved DNA-binding motif Nature. 346:240-4, 1990
62. Gubbay J, Collignon J, Koopman P, Capel B, Economou A, Münsterberg A, Vivian N, Goodfellow P, Lovell-Badge R: A gene mapping to the sex-determining region of the mouse Y chromosome is a member of a novel family of embryonically expressed genes. Nature. 346:245-50, 1990
63. Graham V, Khudyakov J, Ellis P, Pevny L: SOX2 functions to maintain neural progenitor identity. Neuron. 39:749-65, 2003
64. Bylund M, Andersson E, Novitch B G, Muhr J: Vertebrate neurogenesis is counteracted by Sox1-3 activity. Nat Neurosci. 6:1162-8, 2003
65. Pevny L, Placzek M: SOX genes and neural progenitor identity. Curr Opin Neurobiol. 15:7-13, 2005
66. Wegner M, Stolt C C: From stem cells to neurons and glia: a Soxist's view of neural development. Trends Neurosci. 28:583-8, 2005
67. Pennisi D, Bowles J, Nagy A, Muscat G, Koopman P: Mice null for sox18 are viable and display a mild coat defect. Mol Cell Biol. 20:9331-6, 2000
68. Maka M, Stolt C C, Wegner M: Identification of Sox8 as a modifier gene in a mouse model of Hirschsprung disease reveals underlying molecular defect. Dev Biol. 277:155-69, 2005
69. Wilson M E, Yang K Y, Kalousova A, Lau J, Kosaka Y, Lynn F C, Wang J, Mrejen C, Episkopou V, Clevers H C, German M S: The HMG box transcription factor Sox4 contributes to the development of the endocrine pancreas. Diabetes. 54:3402-9, 2005
70. Dewing P, Chiang C W, Sinchak K, Sim H, Fernagut P O, Kelly S, Chesselet M F, Micevych P E, Albrecht K H, Harley V R, Vilain E: Curr Biol. 16:415-20, 2006
71. Matsui T, Kanai-Azuma M, Hara K, Matoba S, Hiramatsu R, Kawakami H, Kurohmaru M, Koopman P, Kanai Y: Redundant roles of Sox17 and Sox18 in postnatal angiogenesis in mice. J Cell Sci. 119:3513-26, 2006
72. O'Donnell M, Hong C S, Huang X, Delnicki R J, Saint-Jeannet J P: Functional analysis of Sox8 during neural crest development in Xenopus. Development. 133:3817-26, 2006
73. Bergsland M, Werme M, Malewicz M, Perlmann T, Muhr J: The establishment of neuronal properties is controlled by Sox4 and Sox11. Genes Dev. 20:3475-86, 2006
74. Smits P, Li P, Mandel J, Zhang Z, Deng J M, Behringer R R, de Crombrugghe B, Lefebvre V: The transcription factors L-Sox5 and Sox6 are essential for cartilage formation. Dev Cell. 1:277-90, 2001
75. Yi Z, Cohen-Barak O, Hagiwara N, Kingsley P D, Fuchs D A, Erickson D T, Epner E M, Palis J, Brilliant M H: Sox6 directly silences epsilon globin expression in definitive erythropoiesis. PLoS Genet. 2:e14, 2006
76. Dumitriu B, Patrick M R, Petschek J P, Cherukuri S, Klingmuller U, Fox P L, Lefebvre V: Sox6 cell-autonomously stimulates erythroid cell survival, proliferation, and terminal maturation and is thereby an important enhancer of definitive erythropoiesis during mouse development. Blood. 108:1198-207, 2006
77. Stolt C C, Schlierf A, Lommes P, Hillgartner S, Werner T, Kosian T, Sock E, Kessaris N, Richardson W D, Lefebvre V, Wegner M: SoxD proteins influence multiple stages of oligodendrocyte development and modulate SoxE protein function. Dev Cell. 11:697-709, 2006
78. Hagiwara N, Klewer S E, Samson R A, Erickson D T, Lyon M F, Brilliant M H: Sox6 is a candidate gene for p100H myopathy, heart block, and sudden neonatal death. Proc Natl Acad Sci USA. 97:4180-5, 2000
79. Cohen-Barak O, Yi Z, Hagiwara N, Monzen K, Komuro I, Brilliant M H: Sox6 regulation of cardiac myocyte development. Nucleic Acids Res. 31:5941-8, 2003
80. Tsukahara K, Yamamoto H, Okayama H: An RNA binding protein negatively controlling differentiation in fission yeast. Mol Cell Biol. 18:4488-98, 1998
81. Yamamoto H, Tsukahara K, Kanaoka Y, Jinno S, Okayama H: Isolation of a mammalian homologue of a fission yeast differentiation regulator. Mol Cell Biol. 19:3829-41, 1999
82. Hosoda T, Bearzi C, Yasuzawa-Amano S, Amano K, Cheng W, Rota M, Kajstura J, Anversa P, Leri A: Genetic marking of human cardiac stem cells. Submitted, 2008
83. Davidson J S, Baumgarten I M, Harley E H: Reversible inhibition of intercellular junctional communication by glycyrrhetinic acid. Biochem Biophys Res Commun. 134: 29-36, 1986.
84. Takeda Y, Ward S M, Sanders K M, Koh S D: Effects of the gap junction blocker glycyrrhetinic acid on gastrointestinal smooth muscle cells. Am J Physiol Gastrointest Liver Physiol. 288:G832-41, 2005
85. Perez-Alcala S, Nieto M A, Barbas J A: LSox5 regulates RhoB expression in the neural tube and promotes generation of the neural crest. Development. 131:4455-65, 2004
86. Melichar H J, Narayan K, Der S D, Hiraoka Y, Gardiol N, Jeannet G, Held W, Chambers C A, Kang J: Regulation of gammadelta versus alphabeta T lymphocyte differentiation by the transcription factor SOX13. Science. 315:230-3, 2007
87. Lai T, Jabaudon D, Molyneaux B J, Azim E, Arlotta P, Menezes J R, Macklis J D: SOX5 Controls the Sequential Generation of Distinct Corticofugal Neuron Subtypes. Neuron. 57:232-247, 2008
88. Dunn T L, Mynett-Johnson L, Wright E M, Hosking B M, Koopman P A, Muscat G E: Sequence and expression of Sox-18 encoding a new HMG-box transcription factor. Gene. 161:223-5, 1995
89. Zhang C, Basta T, Klymkowsky M W: SOX7 and SOX18 are essential for cardiogenesis in Xenopus. Dev Dyn. 234: 878-91, 2005

90. Sakamoto Y, Hara K, Kanai-Azuma M, Matsui T, Miura Y, Tsunekawa N, Kurohmaru M, Saijoh Y, Koopman P, Kanai Y: Redundant roles of Sox17 and Sox18 in early cardiovascular development of mouse embryos. Biochem Biophys Res Commun. 360:539-44, 2007
91. Liu Y, Asakura M, Inoue H, Nakamura T, Sano M, Niu Z, Chen M, Schwartz R J, Schneider M D: Sox17 is essential for the specification of cardiac mesoderm in embryonic stem cells. Proc Natl Acad Sci USA. 104:3859-64, 2007
92. Rota M, Kajstura J, Hosoda T, Bearzi C, Vitale S, Esposito G, Iaffaldano G, Padin-Iruegas M E, Gonzalez A, Rizzi R, Small N, Muraski J, Alvarez R, Chen X, Urbanek K, Bolli R, Houser S R, Leri A, Sussman M A, Anversa P: Bone marrow cells adopt the cardiomyogenic fate in vivo. Proc Natl Acad Sci USA. 104:17783-8, 2007a
93. Vinken M, Vanhaecke T, Papeleu P, Snykers S, Henkens T, Rogiers V: Connexins and their channels in cell growth and cell death. Cell Signal. 18:592-600, 2006
94. Hervé J C, Bourmeyster N, Sarrouilhe D, Duffy H S: Gap junctional complexes: from partners to functions. Prog Biophys Mol Biol. 94:29-65, 2007
95. Meşe G, Richard G, White T W: Gap junctions: basic structure and function. J Invest Dermatol. 127:2516-24, 2007
96. Cancelas J A, Koevoet W L, de Koning A E, Mayen A E, Rombouts E J, Ploemacher R E: Connexin-43 gap junctions are involved in multiconnexin-expressing stromal support of hemopoietic progenitors and stem cells. Blood. 96:498-505, 2000
97. Montecino-Rodriguez E, Dorshkind K: Regulation of hematopoiesis by gap junction-mediated intercellular communication. J Leukoc Biol. 70:341-7, 2001
98. Rosendaal M, Jopling C: Hematopoietic capacity of connexin43 wild-type and knock-out fetal liver cells not different on wild-type stroma. Blood. 101:2996-8, 2003
99. Huettner J E, Lu A, Qu Y, Wu Y, Kim M, McDonald J W: Gap junctions and connexon hemichannels in human embryonic stem cells. Stem Cells. 24:1654-67, 2006
100. Willert K, Brown J D, Danenberg E, Duncan A W, Weissman I L, Reya T, Yates J R 3rd, Nusse R: Wnt proteins are lipid-modified and can act as stem cell growth factors. Nature. 423:448-52, 2003
101. Nusse R: Wnts and Hedgehogs: lipid-modified proteins and similarities in signaling mechanisms at the cell surface. Development. 130:5297-305, 2003
102. Wang H Y, Malbon C C: Wnt signaling, Ca2+, and cyclic GMP: visualizing Frizzled functions. Science. 300:1529-30, 2003
103. Fujino T, Asaba H, Kang M J, Ikeda Y, Sone H, Takada S, Kim D H, Ioka R X, Ono M, Tomoyori H, Okubo M, Murase T, Kamataki A, Yamamoto J, Magoori K, Takahashi S, Miyamoto Y, Oishi H, Nose M, Okazaki M, Usui S, Imaizumi K, Yanagisawa M, Sakai J, Yamamoto T T: Low-density lipoprotein receptor-related protein 5 (LRP5) is essential for normal cholesterol metabolism and glucose-induced insulin secretion. Proc Natl Acad Sci USA. 100:229-34, 2003
104. Daniels D L, Eklof Spink K, Weis W I: beta-catenin: molecular plasticity and drug design. Trends Biochem Sci. 26:672-8, 2001
105. Gottardi C J, Gumbiner B M: Adhesion signaling: how beta-catenin interacts with its partners. Curr Biol. 11:R792-4, 2001
106. Huber O, Korn R, McLaughlin J, Ohsugi M, Herrmann B G, Kemler R: Nuclear localization of beta-catenin by interaction with transcription factor LEF-1. Mech Dev. 59:3-10, 1996
107. Hsu S C, Galceran J, Grosschedl R: Modulation of transcriptional regulation by LEF-1 in response to Wnt-1 signaling and association with beta-catenin. Mol Cell Biol. 18:4807-18, 1998
108. Novak A, Dedhar S: Signaling through beta-catenin and Lef/Tcf. Cell Mol Life Sci. 56:523-37, 1999
109. Naito A T, Shiojima I, Akazawa H, Hidaka K, Morisaki T, Kikuchi A, Komuro I: Developmental stage-specific biphasic roles of Wnt/beta-catenin signaling in cardiomyogenesis and hematopoiesis. Proc Natl Acad Sci USA. 103:19812-7, 2006
110. Kwon C, Arnold J, Hsiao E C, Taketo M M, Conklin B R, Srivastava D: Canonical Wnt signaling is a positive regulator of mammalian cardiac progenitors. Proc Natl Acad Sci USA. 104:10894-9, 2007
111. Nakamura T, Sano M, Songyang Z, Schneider M D: A Wnt- and beta-catenin-dependent pathway for mammalian cardiac myogenesis. Proc Natl Acad Sci USA. 100:5834-9, 2003
112. Koyanagi M, Haendeler J, Badorff C, Brandes R P, Hoffmann J, Pandur P, Zeiher A M, Kuhl M, Dimmeler S: Non-canonical Wnt signaling enhances differentiation of human circulating progenitor cells to cardiomyogenic cells. J Biol Chem. 280:16838-42, 2005
113. Koyanagi M, Bushoven P, Iwasaki M, Urbich C, Zeiher A M, Dimmeler S: Notch signaling contributes to the expression of cardiac markers in human circulating progenitor cells. Circ Res. 101:1139-45, 2007
114. Rota M, LeCapitaine N, Hosoda T, Boni A, De Angelis A, Padin-Iruegas M E, Esposito G, Vitale S, Urbanek K, Casarsa C, Giorgio M, Lüscher T F, Pelicci P G, Anversa P, Leri A, Kajstura J: Diabetes promotes cardiac stem cell aging and heart failure, which are prevented by deletion of the p66shc gene. Circ Res. 99:42-52, 2006
115. Boni A, Nascimbene A, Urbanek K, Delucchi F, Gonzalez A, Siggins R, Amano K, Yasuzawa-Amano S, Ojaimi C, Rota M, Hosoda T, Anversa P, Kajstura J, Leri A: Notch1 receptor enhances myocyte differentiation of cardiac progenitor cells and myocardial regeneration after infarction. Submitted, 2008.
116. Gonzalez A, Rota M, Nurzynska D, Misao Y, Tillmanns J, Ojaimi C, Padin-Iruegas M E, Müller P, Esposito G, Bearzi C, Vitale S, Dawn B, Math S, Baker M, Hintze T H, Bolli R, Urbanek K, Hosoda T, Anversa P, Kajstura J, Leri A: Activation of Cardiac Progenitor Cells Reverses the Failing Heart Senescent Phenotype and Prolongs Lifespan. Circ Res. 102: 597-606, 2008.
117. Sinner D, Rankin S, Lee M, Zorn A M: Sox17 and beta-catenin cooperate to regulate the transcription of endodermal genes. Development. 131:3069-80, 2004
118. Related Articles, Links Wallenstein S, Zucker C L, Fleiss J L: Some statistical methods useful in circulation research. Circ Res. 47:1-9, 1980
119. Berenson M L, Levine D M, Rindskopf D: Applied statistics. Prentice Hall, Englewood Cliffs. 362-418, 1988
120. Rota M, Hosoda T, De Angelis A, Arcarese M L, Esposito G, Rizzi R, Tillmanns J, Tugal D, Musso E, Rimoldi O, Bearzi C, Urbanek K, Anversa P, Leri A, Kajstura J: The young mouse heart is composed of myocytes heterogeneous in age and function. Circ Res. 101:387-99, 2007b
121. Tillmanns J, Rota M, Hosoda T, Misao Y, Esposito G, Gonzalez A, Vitale S, Parolin C, Yasuzawa-Amano S, Muraski J, De Angelis A, Lecapitaine N, Siggins R W, Loredo M, Bearzi C, Bolli R, Urbanek K, Leri A, Kajstura J, Anversa P: Formation of large coronary arteries by cardiac progenitor cells. Proc Natl Acad Sci USA. 105:1668-73, 2008

The invention claimed is:

1. A method for regenerating damaged myocardium in a subject in need thereof comprising:
   (a) administering cardiac stem cells to an area of damaged myocardium in the subject, wherein the cardiac stem cells differentiate into myocytes, smooth muscle cells, and endothelial cells after their administration, thereby regenerating the damaged myocardium; and
   (b) administering a transgene encoding miR-499 to the regenerated myocardium, wherein the regenerated myocardium exhibits the functional characteristics of adult myocardium following transgene administration.

2. The method of claim 1, wherein said transgene is administered by providing a vector encoding said transgene.

3. The method of claim 1, wherein the cardiac stem cells are c-kit positive and lineage negative.

4. The method of claim 1, wherein the cardiac stem cells are autologous.

5. The method of claim 2, wherein the vector is a lentiviral vector.

6. The method of claim 2, wherein said vector comprises a promoter operably linked to the transgene.

7. The method of claim 6, wherein said promoter is a cytomegalovirus promoter.

8. The method of claim 2, wherein the vector is an adenoviral vector.

9. The method of claim 1, wherein miR-499 comprises a sequence of SEQ ID NO: 5.

10. The method of claim 1, wherein said cardiac stem cells are administered to the border zone of the damaged myocardium.

11. The method of claim 1, wherein said cardiac stem cells are administered by an intramyocardial or intraarterial injection.

12. The method of claim 1, wherein said cardiac stem cells are administered by a catheter system.

13. The method of claim 1, wherein said transgene is administered in a lipid-based delivery vehicle.

14. The method of claim 1, wherein said transgene is a polynucleotide comprising a miR-499 sequence.

15. The method of claim 14, wherein said polynucleotide comprises a sequence of SEQ ID NO: 5.

16. The method of claim 1, wherein the subject is suffering from a myocardial infarction.

17. The method of claim 1, wherein the subject is human.

18. The method of claim 1, wherein the transgene is administered by injection into the regenerated myocardium.

19. The method of claim 1, wherein the transgene is administered by a catheter system.

* * * * *